(12) United States Patent
Jacobsen et al.

(10) Patent No.: US 6,271,165 B1
(45) Date of Patent: Aug. 7, 2001

(54) CATALYST COMPONENT DISPERSION COMPRISING AN IONIC COMPOUND AND SOLID ADDITION POLYMERIZATION CATALYSTS CONTAINING THE SAME

(75) Inventors: Grant B. Jacobsen, Houston, TX (US); Pierre H. H. Loix, Wellen; Theo J. P. Stevens, Ham, both of (BE)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/297,422

(22) PCT Filed: Dec. 1, 1997

(86) PCT No.: PCT/US97/21875

§ 371 Date: Jun. 21, 1999

§ 102(e) Date: Jun. 21, 1999

(87) PCT Pub. No.: WO98/27119

PCT Pub. Date: Jun. 25, 1998

Related U.S. Application Data

(63) Continuation-in-part of application No. 08/768,518, filed on Dec. 18, 1996, now Pat. No. 5,783,512.

(51) Int. Cl.$^7$ .............................. B10J 31/22; B10J 31/38; C08F 4/12; C08F 4/16
(52) U.S. Cl. .................. 502/104; 502/117; 502/118; 502/124; 502/125; 502/152; 502/155; 502/156; 502/158; 526/127; 526/133; 526/352; 526/160; 526/943
(58) Field of Search ...................... 502/124, 150, 502/152, 155, 156, 158, 167, 103, 117, 118, 125, 108; 526/127, 133, 160, 101, 948

(56) References Cited

U.S. PATENT DOCUMENTS

| | | |
|---|---|---|
| 4,923,833 | 5/1990 | Kioka et al. . |
| 5,064,802 | 11/1991 | Stevens et al. . |
| 5,444,134 | 8/1995 | Matsumoto . |
| 5,807,938 | 9/1998 | Kaneko et al. . |
| 5,861,352 | 1/1999 | Gila et al. . |

FOREIGN PATENT DOCUMENTS

| | | |
|---|---|---|
| WO 91/09882 | 7/1991 | (WO) . |
| WO 93/11172 | 6/1993 | (WO) . |
| WO 94/03509 | 2/1994 | (WO) . |
| WO 94/03506 * | 2/1994 | (WO) . |
| WO 94/07927 | 4/1994 | (WO) . |
| WO 96/04319 | 2/1996 | (WO) . |
| WO 96/28480 | 9/1996 | (WO) . |

\* cited by examiner

Primary Examiner—David W. Wu
Assistant Examiner—R. Harlan

(57) ABSTRACT

This invention relates to supported and nonsupported catalyst components comprising (a) an ionic compound comprising (a)(1) a cation and (a)(2) an anion having up to 100 nonhydrogen atoms and the anion containing at least one subtituent comprising a moiety having an active hydrogen reacted with (c) an organometal or metalloid compound wherein the metal or metalloid is selected from Groups 2, 12, 13, or 14 of the Periodic Table of the Elements, and, optionally, (b) a transition metal compound, (d) a support material, and/or a diluent. Included are methods for preparation of the catalyst components, catalysts, reaction products and dispersions thereof, as well as polymerization process using the catalyst.

48 Claims, 3 Drawing Sheets

CATALYST COMPONENT DISPERSION COMPRISING AN IONIC COMPOUND AND SOLID ADDITION POLYMERIZATION CATALYSTS CONTAINING THE SAME

CROSS REFERENCE STATEMENT

This application claims the benefit of priority under 35 U.S.C. §371 of PCT/US97/21875, filed Dec. 1, 1997, which was published under PCT Article 21(2) in English, and which is a continuation-in-part of U.S. application Ser. No. 08/768,518, filed Dec. 18, 1996, now U.S. Pat. No. 5,783, 512.

FIELD OF THE INVENTION

This invention relates to a catalyst component dispersion comprising an ionic compound in solid form, to a nonsupported solid catalyst comprising a transition metal compound, an ionic compound, and an organometal compound, to a supported solid catalyst comprising a transition metal compound, an ionic compound, an organometal compound, and a support material, to a method for preparing the catalyst component dispersion, to a method for preparing the solid catalysts, to a method for activating a catalyst suitable for addition polymerization, and to an addition polymerization process using the solid catalysts.

BACKGROUND OF THE INVENTION

Homogeneous ionic transition metal catalysts are known for their high catalytic activity in addition polymerizations, especially those of olefins and diolefins, and are capable of providing olefinic polymers of narrow molecular weight distributions and, for example when ethylene is copolymerized with a further alpha-olefin, narrow comonomer distributions. Under polymerization conditions where polymer is formed as solid particles, for example, in gas phase or slurry phase polymerizations, these homogeneous (soluble) catalysts form polymer deposits on reactor walls and stirrers which deposits should be removed frequently as they prevent an efficient heat-exchange necessary for cooling the reactor contents, prevent the regular or continuous removal of polymer from the reactor, and cause excessive wear of the moving parts in the reactor. The polymers produced by these soluble catalysts further have undesirable particle characteristics such as a low bulk density which limits the commercial utility of both the polymer and the process. Therefore, there is a need to provide catalysts that would overcome such problems.

Several supported catalysts have been proposed for use in particle forming polymerization processes. Support materials in the prior art are typically employed in combination with catalytic components to obtain the formation of polymer particles of desirable particle size and morphology. Secondly, support materials are used to increase catalytic activity per unit of active components by depositing such components on a support material having a relatively high surface area. Furthermore, support materials are employed for anchoring thereon the catalytic components to avoid the presence of significant amounts of catalyst which under particle forming polymerization conditions becomes solubilized and gives rise to particles of undesired size and morphology said particles contributing to the formation of polymer deposits at reactor walls and other moving parts in the reactor.

EP-327649 and EP-725086 describe solid catalysts using alumoxanes as cocatalyst. EP-327649 relates to a nonsupported olefin polymerization catalyst composed of a transition metal compound and an alumoxane having an average particle size of 5 to 200 micrometers and a specific surface area of 20 to 1,000 m$^2$/g. EP-725086 describes a solid component of a catalyst for ethylene and alpha-olefins (co)polymerization comprising a metallocene supported on an inorganic solid carrier, where a carbon atom of one of the $\eta^5$-cyclopentadienyl rings coordinated to the transition metal is covalently bonded to a metal atom of the inorganic solid carrier. This solid component is typically used with an organic aluminum oxy-derivative which is usually alumoxane.

Supported nonalumoxane catalysts are disclosed, for example, in EP-418044, EP-522581, WO-91/09882, WO-94/03506, WO-9403509, and WO-9407927. These describe supported catalysts obtained by combining a transition metal compound, an activator component comprising a cation capable of reacting with a transition metal compound and a bulky, labile anion capable of stabilizing the metal cation formed as a result of reaction between the metal compound and the activator component, and a catalyst support material. In EP-522581 and WO-9407927 additionally an organometal compound, typically an organoaluminum compound is employed.

EP-727443 describes an olefin polymerization catalyst obtainable by contacting a transition metal compound, an organometallic compound, and a solid catalyst component comprising a carrier and an ionized ionic compound capable of forming a stable anion on reaction with said transition metal compound, wherein said ionized ionic compound comprises a cationic component and an anionic component and said cationic component is fixed on the surface of the carrier.

WO-96/04319 describes a catalyst composition comprising a metal oxide support having covalently bound to the surface thereof directly through the oxygen atom of the metal oxide, an activator anion that is also ionically bound to a catalytically active transition metal compound.

WO-93/11172 relates to polyanionic moieties comprising a plurality of noncoordinating anionic groups pendant from and chemically bonded to a core component. The core component may be a cross-linked polystyrene or polydivinylbenzene polymeric core or a polyanionic Lewis basic core substrate reactable with a Lewis acid. The polyanionic moieties are used in a noncoordinating association with cationic transition metal compounds.

Copending U.S. application Ser. No. 08/610,647, filed Mar. 4, 1996, U.S. Pat. No. 5,834,393 corresponding to WO-96/28480, describes supported catalyst components comprising a support material, an organometal compound, an activator compound comprising a cation which is capable of reacting with a transition metal compound to form a catalytically active transition metal complex and a compatible anion having up to 100 nonhydrogen atoms and containing at least one substituent comprising a moiety having an active hydrogen. When combined with a transition metal compound, the resulting supported catalysts are very useful addition polymerization catalysts.

It would be desirable to provide a solid catalyst and solid catalyst dispersions, and components or precursors therefore which do not require an alumoxane component and which can be used in particle formation polymerization processes without requiring a support material.

It would also be desirable to provide a solid catalyst, including precursors therefor, which when used in a polymerization process are capable of producing polymers at good catalyst efficiencies.

It is a further object to provide a solid catalyst, including precursors therefore which when used in a particle forming polymerization process give reduced amounts of particles of undesired size and morphology. It is yet a further object to provide a solid catalyst, including precursors therefore, which when used in a particle forming polymerization process prevents or largely removes the problem of formation of polymer deposits at reactor walls and other moving parts in the reactor.

It is yet a further object to provide a solid catalyst and polymerization process that is capable of forming polymers in the form of free flowing powder or particles.

It is another object to provide a method for making a solid catalyst without requiring recovery or purification steps.

It is a further object to provide a solid catalyst which further comprises a support material.

One or several of these objects are accomplished by the embodiments of the present invention described hereinafter.

SUMMARY OF THE INVENTION

In one aspect of this invention there is provided a dispersion of a supported catalyst component comprising (a) an ionic compound comprising (a)(1) a cation and (a)(2) an anion having up to 100 nonhydrogen atoms and the anion containing at least one substituent comprising a moiety having an active hydrogen and (d) a support material, wherein the supported catalyst component is in solid form dispersed in a diluent in which both (a) and (d) are insoluble or sparingly soluble, and wherein, (i) the support material is a pretreated support material and in the supported catalyst component the anion (a)(2) is not chemically bonded to the support (d), or (ii) the ionic compound has a solubility in toluene at 22° C. of at least 0.1 weight percent, the support material used is a support material containing tethering groups and in the supported catalyst component the anion (a)(2) is chemically bonded to the support (d).

In a related aspect there is provided a dispersion of a nonsupported catalyst component comprising (a) an ionic compound comprising (a)(1) a cation and (a)(2) an anion having up to 100 nonhydrogen atoms and the anion containing at least one substituent comprising a moiety having an active hydrogen, wherein (a) is in solid form in the absence of a support material and is dispersed in a diluent in which (a) is insoluble or sparingly soluble.

Desirable embodiments of the aforementioned dispersions are those wherein the catalyst component further comprises (b) a transition metal compound and wherein the catalyst component is a substantially inactive catalyst precursor; or wherein the catalyst component further comprises (c) an organometal or metalloid compound wherein the metal or metalloid is selected from the Groups 1–14 of the Periodic Table of the Elements and the catalyst component is a reaction product of (a) and (c), while in other desirable embodiments the catalyst component excludes (b) a transition metal compound, excludes (c) an organometal or metalloid compound wherein the metal or metalloid is selected from the Groups 1–14 of the Periodic Table of the Elements, or excludes both (b) and (c).

In another aspect of this invention there is provided a nonsupported catalyst comprising, in the absence of a support material, (a) an ionic compound comprising (a)(1) a cation and (a)(2) an anion having up to 100 nonhydrogen atoms and the anion containing at least one substituent comprising a moiety having an active hydrogen, (b) a transition metal compound, and (c) an organometal or metalloid compound wherein the metal is selected from the Groups 1–14 of the Periodic Table of the Elements.

In an other aspect of this invention there is provided a supported solid catalyst comprising (a) an ionic compound comprising (a)(1) a cation and (a)(2) an anion having up to 100 nonhydrogen atoms and the anion containing at least one substituent comprising a moiety having an active hydrogen, (b) a transition metal compound, (c) an organometal or metalloid compound wherein the metal or metalloid is selected from the Groups 1–14 of the Periodic Table of the Elements, and (d) a support material, wherein, (i) the support material is a pretreated support material and in the supported catalyst component the anion (a)(2) is not chemically bonded to the support (d), or (ii) the ionic compound has a solubility in toluene at 22° C. of at least 0.1 weight percent, the support material used is a support material containing tethering groups and in the supported catalyst component the anion (a)(2) is chemically bonded to the support (d); and, wherein the solid catalyst is obtained by combining components (a), (b), (c), and (d) in any order, and wherein, during at least one step in the preparation of the solid catalyst, component (a) is dissolved in a diluent in which (a) is soluble, optionally in the presence of one or more of components (b), (c), and (d) or the contact product of (a) with such one or more of (b), (c), and (d), and then is converted into solid form.

In the aforementioned aspects relating to a nonsupported catalyst and to a supported catalyst, desirable embodiments are those wherein the anion (a)(2) corresponds to Formula (II):

 (II)

wherein:

M' is a metal or metalloid selected from Groups 5–15 of the Periodic Table of the Elements;

Q independently in each occurrence is selected from the group consisting of hydride, dihydrocarbylamido, halide, hydrocarbyloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion in each of these groups preferably having from 1 to 20 carbons, with the proviso that in not more than one occurrence is Q halide; G is a polyvalent hydrocarbon radical having r+1 valencies bonded to M' and r groups (T—H);

the group (T—H) is a radical wherein T comprises O, S, NR, or PR, the O, S, N of P atom of which is bonded to hydrogen atom H wherein R is a hydrocarbyl radical, a trihydrocarbylsilyl radical, a trihydrocarbyl germyl radical or hydrogen;

m is an integer from 1 to 7;

n is an integer from 0 to 7;

q is an integer of 0 or 1;

r is an integer from 1 to 3;

z is an integer from 1 to 8;

d is an integer from 1 to 7; and n+z−m=d, and where the cation (a)(1) of ionic compound (a) is represented by the following general formula:

wherein:
L* is a nitrogen, oxygen. sulfur or phosphorus containing Lewis base containing from one to three $C_{10-40}$ alkyl groups with a total of from 12 to 100 carbons.

When the catalysts of the present invention include a support material (d) the versatility of the catalyst is improved. Employing a support material allows the particle size of the solid catalyst to be varied between wider ranges.

In another aspect of this invention there is provided a method for preparing a dispersion of a supported catalyst component comprising (a) an ionic compound comprising (a)(1) a cation and (a)(2) an anion having up to 100 nonhydrogen atoms and the anion containing at least one substituent comprising a moiety having an active hydrogen, and (d) a support material, where the supported catalyst component is in solid form dispersed in a diluent in which both (a) and (d) are insoluble or sparingly soluble, the method comprising converting a solution of the ionic compound (a) in a diluent in which (a) is soluble in the presence of the support material into a dispersion comprising component (a) in solid form, and wherein,
(i) the support material used is a pretreated support material and, in the supported catalyst component, the anion (a)(2) is not chemically bonded to the support (d), or
(ii) the ionic compound used has a solubility in toluene at 22° C. of at least 0.1 weight percent, the support material used is a support material containing tethering groups and, in the supported catalyst component, the anion (a)(2) is chemically bonded to the support (d).

In another aspect of this invention there is provided a method for preparing a dispersion of a nonsupported catalyst component comprising converting a solution of an ionic compound (a) comprising (a)(1) a cation and (a)(2) an anion having up to 100 nonhydrogen atoms and the anion containing at least one substituent comprising a moiety having an active hydrogen, in a diluent in which (a) is soluble in the absence of a support material into a dispersion comprising component (a) in solid form.

In another aspect of this invention there is provided a method for preparing a solid catalyst comprising combining, in any order, (a) an ionic compound comprising (a)(1) a cation and (a)(2) an anion having up to 100 nonhydrogen atoms and the anion containing at least one substituent comprising a moiety having an active hydrogen, (b) a transition metal compound, (c) an organometal or metalloid compound wherein the metal or metalloid is selected from the Groups 1–14 of the Periodic Table of the Elements, and, optionally, (d) a support material, wherein during at least one step in the preparation of the solid catalyst, component (a) is dissolved in a diluent in which (a) is soluble to produce a solution of (a), optionally in the presence of one or more of components (b), (c), and (d) or the contact product of (a) with such one or more of (b), (c), and (d), and then is converted into solid form, optionally followed by recovering the solid catalyst in dry particulate form, wherein, when a support material (d) is present,
(i) the support material used is a pretreated support material and in the supported catalyst the anion (a)(2) is not chemically bonded to the support (d), or
(ii) the ionic compound used has a solubility in toluene at 22° C. of at least 0.1 weight percent, the support material used is a support material containing tethering groups and in the supported catalyst the anion (a)(2) is chemically bonded to the support (d).

A highly desirable embodiment of this method for preparing a solid catalyst is that wherein the support material used is a pretreated support material with a pore volume of from 0.1 to 5 cm³/g and in the supported catalyst the anion (a)(2) is not chemically bonded to the support ((1), and wherein the volume of the solution of (a), optionally in the presence of one or both of (b) and (c), is from 20 volume percent to 200 volume percent of the total pore volume of the support material used, and wherein the solid catalyst is produced by adding the solution of (a) to substantially dry pretreated support material, followed by removal of the diluent.

An alternative embodiment of this method for preparing a solid catalyst is that wherein during the at least one step in the preparation of the solid catalyst, a dispersion comprising component (a) in solid form is generated by cooling a solution of (a) in a diluent in which (a) is soluble, by contacting a solution of (a) in a diluent in which (a) is soluble with a diluent in which (a) is insoluble or sparingly soluble, by evaporating diluent from a solution of (a), by adding one or more precipitating agents to a solution of (a), or a combination of two or more of these techniques.

In another aspect of this invention there is provided a method for activating a substantially inactive catalyst precursor to form a catalyst suitable for addition polymerization wherein a substantially inactive catalyst precursor comprising (a) an ionic compound comprising (a)(1) a cation and (a)(2) an anion having up to 100 nonhydrogen atoms and the anion containing at least one substituent comprising a moiety having an active hydrogen, (b) a transition metal compound, and, optionally, (d) a support material, is contacted with (c) an organometal or metalloid compound, where the metal or metalloid is selected from Groups 1–14 of the Periodic Table of the Elements, to form an active catalyst.

In another aspect of this invention there is provided and addition polymerization process wherein one or more addition polymerizable monomers are contacted with one of the aforementioned solid catalysts under addition polymerization conditions.

In another aspect of this invention there is provided an ionic compound (a) comprising (a)(1) a cation and (a)(2) an anion having up to 100 nonhydrogen atoms and the anion containing at least one substituent comprising a moiety having an active hydrogen, where the cation (a)(1) is represented by the following general formula:

[L*—H]⁺, wherein:
L* is a nitrogen, oxygen, sulfur or phosphorus containing Lewis base containing from one to three $C_{10-40}$ alkyl groups with a total of from 12 to 100 carbons, and where the anion (a)(2) corresponds to Formula (II):

$$[M'^{m+}Q_n(G_q(T{-}H)_r)_z]^{d-} \qquad (II)$$

wherein:
M' is a metal or metalloid selected from Groups 5–15 of the Periodic Table of the Elements;
Q independently in each occurrence is selected from the group consisting of hydride, dihydrocarbylamido, halide, hydrocarbyloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion in each of these groups preferably having from 1 to 20 carbons, with the proviso that in not more than one occurrence is Q halide; G is a polyvalent hydrocarbon radical having r+1 valencies bonded to M' and r groups (T—H);

the group (T—H) is a radical wherein T comprises O, S, NR, or PR, the O, S, N or P atom of which is bonded to hydrogen atom H wherein R is a hydrocarbyl radical, a trihydrocarbylsilyl radical, a trihydrocarbyl germyl radical or hydrogen;

m is an integer from 1 to 7;

n is an integer from 0 to 7;

q is an integer of 0 or 1;

r is an integer from 1 to 3;

z is an integer from 1 to 8;

d is an integer from 1 to 7; and n+z−m=d.

Surprisingly, it has been found that the ionic compound (a) can be advantageously used in a solid form dispersed in a diluent in which (a) is insoluble or sparingly soluble (the diluent in which (a) is insoluble or sparingly soluble is also referred to as "nonsolvent"; the diluent in which (a) is soluble is also referred to as "solvent"). By use of the dispersed solid ionic compound (a) in association with transition metal compound (b) and organometal compound (c) an active solid particulate addition polymerization catalyst results, preferably in dispersed form. Such a solid dispersed catalyst advantageously can be used in a particle forming polymerization process, such as a slurry or gas phase polymerization process, without requiring an additional support material to produce polymer of the desired particle size and morphology. The solid dispersed catalysts of the present invention can produce polymers in the form of free flowing powder or particles, without causing substantial polymer deposits at reactor walls and other moving parts in the reactors. Free flowing ethylene based polymers and interpolymers preferably have bulk densities of at least about 0.20 g/cm$^3$, and more preferably of at least about 0.25 g/cm$^3$.

In another aspect of this invention there is provided a compound which is the reaction product of (a) an ionic compound described above and (c) an organometal or metalloid compound wherein the metal or metalloid is selected from the Groups 1–14 of the Periodic Table of the Elements. A desirable embodiment is that where the compound corresponds to the formula

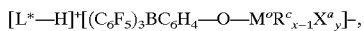

wherein

M° is a metal or metalloid selected from Groups 1–14 of the Periodic Table of the Elements, R$^c$ independently each occurrence is hydrogen or a group having from 1 to 80 nonhydrogen atoms which is hydrocarbyl, hydrocarbylsilyl, or hydrocarbylsilylhydrocarbyl;

X$^a$ is a noninterfering group having from 1 to 100 nonhydrogen atoms which is halo-substituted hydrocarbyl, hydrocarbylamino-substituted hydrocarbyl, hydrocarbyloxy-substituted hydrocarbyl, hydrocarbylamino, di(hydrocarbyl)amino, hydrocarbyloxy or halide;

x is a nonzero integer which may range from 1 to an integer equal to the valence of M°;

y is zero or a nonzero integer which may range from 1 to an integer equal to 1 less than the valence of M°; and x+y equals the valence of M°.

In a further aspect of this invention there is provided a substantially inactive catalyst precursor comprising (a) an ionic compound described above, and (b) a transition metal compound.

DETAILED DESCRIPTION OF THE INVENTION

Figure 1A:
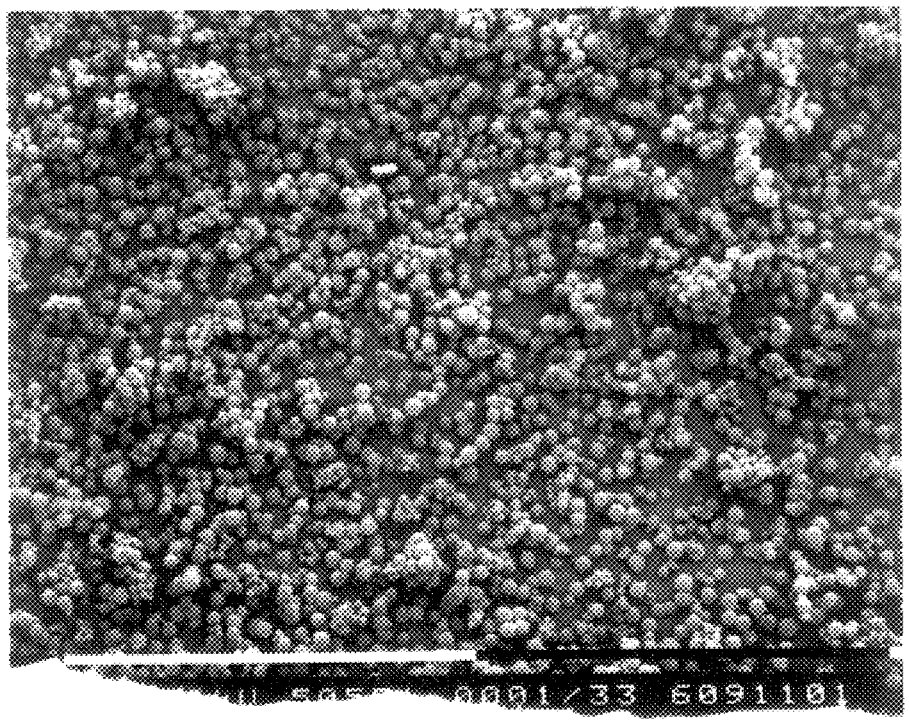
FIG. 1A and FIG. 1B are scanning electron micrographs of slurry produced polyethylene at a magnification of 50 times.

All references herein to elements or metals belonging to a certain Group refer to the Periodic Table of the Elements published and copyrighted by CRC Press, Inc., 1989. Also any reference to the Group or Groups shall be to the Group or Groups as reflected in this Periodic Table of the Elements using the IUPAC system for numbering groups.

The term "nonsupported" as used in the present application means in the absence of a material which typically may be used as a support or carrier in an addition polymerization catalyst, more in particular as an olefin addition polymerization catalyst. Conversely, the term "supported" as used in the present application means in the presence of a material which typically may be used as a support or carrier in an addition polymerization catalyst, more in particular as an olefin addition polymerization catalyst. Where in the present application the term "solid catalyst" is used, it embraces both nonsupported and supported solid catalysts, unless it follows differently from the context.

Where in the present invention a composition is defined by its starting components or starting compounds optionally in combination with certain process steps, such as for example contacting and combining steps, it is meant that the composition encompasses starting components or starting compounds but also the reaction product or reaction products of the starting components or starting compounds to the extent a reaction has taken place.

The dispersion of (a) of the present invention is preferably characterized by an average particle size of (a), as measured by laser diffraction, in the range of from 0.1 to 200 μm, more preferably in the range of from 0.5 to 50 μm. The dispersion of (a) preferably contains from 0.00001 to 10 mole of solid compound (a)/l, more preferably from 0.0001 to 1 mole/l. The particle size of the dispersion of (a) was measured using a Malvern Mastersizer particle size analyzer.

Some ionic compounds (a) to be used in the present invention and their methods of preparation are described in U.S. patent application Ser. No. 08/610,647, filed Mar. 4, 1996 (corresponding to WO-96/28480) which is incorporated herein by reference. Other ionic compounds are more nearly related to those disclosed in U.S. patent application Ser. No., filed [42808A], some of which may be useful in various aspects of this invention. Preferred ionic compounds of this invention have not previously been disclosed, and have the advantage of being highly soluble in the solvents and diluents used in various methods utilizing these ionic compounds, while at the same time the preferred ionic compounds contain a moiety having an active hydrogen. The term used in the anion (a)(2) of the ionic compound "at least one substituent comprising a moiety having an active hydrogen" means in the present application a substituent comprising a hydrogen atom bonded to an oxygen, sulphur, nitrogen or phosphorous atom. The presence of at least one moiety having an active hydrogen in the ionic compound imparts an unprecedented versatility to it in the catalyst arts, for it is capable of entering into various reactions primarily through covalent bonding, such as, for example, bonding to a tethering group, such as, for example, a surface hydroxyl group of a support material, or in forming a reaction product with an organometal or metalloid compound, or in forming a complex or reaction product with a transition metal compound.

When various chemical formulas are used herein to represent various chemical compounds, it should be recognized that the formula is emperical and not necessarily molecular. In particular, with regard to various organometal or metalloid compounds, especially those containing aluminum, and to the various alumoxanes, it is understood that a single emperical formula may be used as is conventional in the catalyst arts to represent what may be various dimers, trimers and other higher oligomers, depending upon the physical environment including various solvents or diluents in which the compound is employed.

The anion (a)(2) comprises a single Group 5–15 element or a plurality of Group 5–15 elements but is preferably a single coordination complex comprising a charge-bearing metal or metalloid core. Preferred anions (a)(2) are those containing a single coordination complex comprising a charge-bearing metal or metalloid core carrying the at least one substituent containing a moiety having an active hydrogen. Suitable metals for the anions of ionic compounds (a) include, but are not limited to, aluminum, gold, platinum and the like. Suitable metalloids include, but are not limited to elements of Groups 13, 14, and 15, of the Periodic Table of Elements, preferably are, boron, phosphorus, and silicon. Ionic compounds which contain anions comprising a coordination complex containing a single boron atom and one or more substituents comprising a moiety having an active hydrogen are preferred. Examples of suitable anions comprising a single Group 5–15 element are disclosed in EP-277 004 and examples of those having a plurality of Group 5–15 elements are disclosed in EP-0 277 003, with the proviso that at least one of the subsituents in the anions described therein is substituted by a substituent comprising a moiety having an active hydrogen, preferably $G_q(T—H)_r$.

Preferably, anions (a)(2) may be represented by a single coordination complex of the following general Formula (II):

wherein:

M' is a metal or metalloid selected from Groups 5–15 of the Periodic Table of the Elements;

Q independently in each occurrence is selected from the group consisting of hydride, dihydrocarbylamido, preferably dialkylamido, halide, hydrocarbyloxide, preferably alkoxide and aryloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion in each of these groups preferably having from 1 to 20 carbons, with the proviso that in not more than one occurrence is Q halide;

G is a polyvalent hydrocarbon radical having r+1 valencies, and preferably a divalent hydrocarbon radical, bonded to M' and r groups (T—H);

the group (T—H) is a radical wherein T comprises O, S, NR, or PR, the O, S, N, or P atom of which is bonded to hydrogen atom H, wherein R is a hydrocarbon radical, a trihydrocarbyl silyl radical, a trihydrocarbyl germyl radical, or hydrogen;

m is an integer from 1 to 7, preferably 3;

n is an integer from 0 to 7, preferably 3;

q is an integer 0 or 1, preferably 1;

r is an integer from 1 to 3, preferably 1;

z is an integer from 1 to 8, preferably 1 or 2;

d is an integer from 1 to 7, preferably 1; and n+z−m=d.

When q is 0 and polyvalent hydrocarbon radical G is not present, T is bound to M'. Preferred boron-containing anions (a)(2) which are particularly useful in this invention may be represented by the following general Formula (III):

wherein:

B is boron in a valence state of 3;

z' is an integer from 1–4, preferably 1 or 2, most preferably 1;

d is 1; and

Q, G, T, H, q, and r are as defined for Formula (II). Preferably, z' is 1 or 2, q is 1, and r is 1.

In the anion (a)(2), the at least one substituent comprising, a moiety having an active hydrogen preferably corresponds to Formula I:

wherein G is a polyvalent hydrocarbon radical, the group (T—H) is a radical wherein T comprises O, S, NR, or PR, the O, S, N, or P atom of which is bonded to hydrogen atom H, wherein R is a hydrocarbyl radical, a trihydrocarbyl silyl radical, a trihydrocarbyl germyl radical, or hydrogen, H is hydrogen, q is 0 or 1, and preferably 1, and r is an integer from 1 to 3, preferably 1. Polyvalent hydrocarbon radical G has r+1 valencies, one valency being associated with a metal or metalloid of the Groups 5–15 of the Periodic Table of the Elements in the anion, the other r valencies of G being attached to r groups (T—H). Preferred examples of G include di- or trivalent hydrocarbon radicals such as: alkylene, arylene, aralkylene, or alkarylene radicals containing from 1 to 20 carbon atoms, more preferably from 2 to 12 carbon atoms. Suitable examples of divalent hydrocarbon radicals G include phenylene, biphenylene, naphthylene, methylene, ethylene, 1,3-propylene, 1,4-butylene, phenylmethylene (—$C_6H_4$—$CH_2$—). The polyvalent hydrocarbyl portion G may be further substituted with radicals that do not negatively impact the effect to be achieved by the present invention. Preferred examples of such noninterfering substituents are alkyl, aryl, alkyl- or aryl-substituted silyl and germyl radicals, and fluoro substituents.

The group (T—H) in the previous formula may be an —OH, —SH, —NRH, or —PRH group, wherein R preferably is a $C_{1-18}$, preferably a $C_{1-12}$, hydrocarbyl radical or hydrogen, and H is hydrogen. Preferred R groups are alkyls, cycloalkyls, aryls, arylalkyls, or alkylaryls of 1 to 18 carbon atoms, more preferably those of 1 to 12 carbon atoms. Alternatively, the group (T—H) comprises an —OH, —SH, —NRH, or —PRH group which are part of a larger functional moiety such as, for example, C(O)—OH, C(S)—OH, C(S)—SH, C(O)—SH, C(O)—NRH, C(S)—NRH, and C(O)—PRH, and C(S)—PRH. Most preferably, the group (T—H) is a hydroxy group, —OH, or an amino group, —NRH.

Very preferred substituents $G_q$(T—H) in anion (a)(2) include hydroxy- and amino-substituted aryl, aralkyl, alkaryl or alkyl groups, and most preferred are the hydroxyphenyls, especially the 3- and 4-hydroxyphenyl groups and 2,4-dihydroxyphenyl, hydroxytolyls, hydroxybenzyls (hydroxymethylphenyl), hydroxybiphenyls, hydroxynaphthyls, hydroxycyclohexyls, hydroxymethyls, and hydroxypropyls, and the corresponding amino-substituted groups, especially those substituted with —NRH wherein R is an alkyl or aryl radical having from 1 to 10 carbon atoms, such as for example methyl, ethyl, propyl, i-propyl, n-, i-, or t-butyl, pentyl, hexyl, heptyl, octyl, nonyl, and decyl, phenyl, benzyl, tolyl, xylyl, naphthyl, and biphenyl.

Illustrative, but not limiting, examples of anions (a)(2) of ionic compounds to be used in the present invention are boron-containing anions such as:
triphenyl(hydroxyphenyl)borate, triphenyl(2,4-dihydroxyphenyl)borate,
tri(p-tolyl )(hydroxyphenyl )borate,
tris-(pentafluorophenyl )(hydroxyphenyl )borate, tris-(2,4-dimethylphenyl)(hydroxyphenyl)borate,
tris-(3,5-dimethylphenyl)(hydroxyphenyl)borate,
tris-(3,5-di-trifluoromethyl-phenyl)(hydroxyphenyl)borate, tris(pentafluorophenyl)(2-hydroxyethyl)borate, tris (pentafluorophenyl)(4-hydroxybutyl)borate,
tris(pentafluorophenyl)(4-hydroxycyclohexyl)borate, tris (pentafluorophenyl)(4-(4'-hydroxyphenyl)phenyl)borate, tris(pentafluorophenyl)(6-hydroxy-2-naphthyl)borate,
and the like.

Further preferred anions (a)(2) include those containing two substituents containing a moiety having an active hydrogen, for example: diphenyldi(hydroxyphenyl)borate, diphenyldi(2,4-dihydroxyphenyl)borate, di(p-tolyl)di (hydroxyphenyl)borate, di(pentafluorophenyl)di-(hydroxyphenyl)borate, di(2,4-dimethylphenyl) di(hydroxyphenyl)borate, di(3,5-dimethylphenyl)di (hydroxyphenyl)borate, di(3,5-di-trifluoromethylphenyl)di (hydroxyphenyl)borate, di(pentafluorophenyl)di(2-hydroxyethyl)borate, di(pentafluorophenyl)di(4-hydroxybutyl)borate, di(pentafluorophenyl)di(4-hydroxycyclohexyl)borate, di(pentafluorophenyl)di(4-(4'-hydroxyphenyl)phenyl)borate, di(pentafluorophenyl)di(6-hydroxy-2-naphthyl)borate, and the like.

Other preferred anions are those above-mentioned borates wherein the hydroxy functionality is replaced by an amino NHR functionality wherein R preferably is methyl, ethyl, or t-butyl. A highly preferred anion (a)(2) is tris (pentafluorophenyl)(4-hydroxyphenyl)borate.

The cationic portion (a)(1) of the ionic compound is preferably selected from the group consisting of Bronsted acidic cations, especially ammonium and phosphonium cations or sulfonium cations, carbonium cations, silylium cations, oxonium cations, organometallic cations and cationic oxidizing agents. The cations (a)(1) and the anions (a)(2) are used in such ratios as to give a neutral ionic compound.

Bronsted acidic cations may be represented by the following general formula:

wherein:
L is a neutral Lewis base, preferably a nitrogen, phosphorus, oxygen, or sulfur containing Lewis base; and (L—H)⁺ is a Bronsted acid.

Illustrative, but not limiting, examples of Bronsted acidic cations are trihydrocarbyl- and preferably trialkyl-substituted ammonium cations such as triethylammonium, tripropylammonium, tri(n-butyl) ammonium, trimethylammonium,
tri(i-butyl)ammonium, and tri(n-octyl)ammonium. Also suitable are N,N-dialkyl anilinium cations such as N,N-dimethylanilinium, N,N-diethyl-anilinium, N,N-2,4,6-pentamethylanilinium,
N,N-dimethylbenzylammonium and the like; dialkylammonium cations such as di-(i-propyl)ammonium, dicyclohexylammonium and the like; and triarylphosphonium cations such as triphenylphosphonium, tri(methylphenyl) phosphonium,
tri(dimethylphenyl)phosphonium, dimethylsulphonium, diethylsulphonium, and diphenylsulphonium.

In a highly preferred embodiment, the Bronsted acidic cation (a)(1) may be represented by the following general formula:

wherein:
L* is a nitrogen, oxygen, sulfur or phosphorus containing Lewis base which comprises at least one relatively long chain alkyl group. Preferably such L* groups contain from one to three $C_{10-40}$ alkyl groups with a total of from 12 to 100 carbons, more preferably two $C_{10-40}$ alkyl groups and from 21 to 90 total carbons. It is understood that the cation may comprise a mixture of alkyl groups of differing lengths. For example, one suitable cation is the protonated ammonium salt derived from the commercially available long chain amine comprising a mixture of two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT. These preferred cations are described in U.S. provisional application Ser. No. 60/014284, filed Mar. 27, 1996, which is incorporated herein by reference. Ionic compounds (a) comprising the cation [L*—H]⁺ can be easily prepared by subjecting an ionic compound comprising the cation [L—H]⁺ and the anion (a)(2), as prepared in U.S. patent application Ser. No. 08/610,647, filed Mar. 4, 1996 (corresponding to WO-96/28480), to a cation exchange reaction with a [L*—H]⁺ salt.

Generally, the preferred ionic compounds have a solubility in toluene at 22° C. of at least 0.1 weight percent, desirably, of at least 0.3 weight percent, more desirably of at least 1 weight percent, preferably of at least 5 weight percent, more preferably of at least 10 weight percent and in some instances even more than 15 weight percent.

Illustrative, but not limiting examples of the highly preferred cations (a)(1) are
tri-substituted ammonium salts such as: decyldi(methyl) ammonium,
dodecyldi(methyl)ammonium, tetradecyldi(methyl) ammonium,
hexaadecyldi(methyl)ammonium, octadecyldi(methyl) ammonium,
eicosyldi(methyl)ammonium, methyldi(decyl)ammonium,
methyldi(dodecyl)ammonium, methyldi(tetradecyl) ammonium,
methyldi(hexadecyl)ammonium, methyldi(octadecyl) ammonium,
methyldi(eicosyl)ammonium, tridecylammonium, tridodecylammonium,
tritetradecylammonium, trihexadecylammonium, trioctadecylammonium,
trieicosylammonium, decyldi(n-butyl)ammonium, dodecyldi(n-butyl)ammonium, octadecyldi(n-butyl)ammonium, N,N-didodecylanilinium, N-methyl-N-dodecylanilinium, N,N-di(octadecyl)(2,4,6-trimethylanilinium), cyclohexyldi(dodecyl)ammonium, and methyldi(dodecyl)ammonium.

Suitable similarly substituted sulfonium or phosphonium cations such as, di(decyl)sulfonium, (n-butyl)dodecylsulfonium, tridecylphosphonium, di(octadecyl)methylphosphonium, and tri(tetradecyl)phosphonium, may also be named.

Preferred ionic compounds (b) are di(octadecyl)methylammonium tris(pentafluorophenyl)(hydroxyphenyl)borate, octadecyl dimethylammonium tris(pentafluorophenyl)borate and di(octadecyl)(n-butyl)ammonium tris(pentafluorophenyl)(hydroxyphenyl)-borate, as well as the amino (—NHR) analogues of these compounds wherein the hydroxyphenyl group is replaced by the aminophenyl group.

A second type of suitable cation corresponds to the formula: (©)$^+$, wherein (©)$^+$ is a stable carbonium or sylylium ion containing up to 30(nonhydrogen atoms. Suitable examples of cations include tropyllium, triphenylmethylium, benzene(diazonium). Silylium salts have been previously generically disclosed in J. Chem. Soc. Chem. Comm., 1993, 383–384, as well as Lambert, J. B., et. al., Organometallics, 1994, 13, 2430–2443. Preferred silylium cations are triethylsilylium, and trimethylsilylium and ether substituted adducts thereof.

Another suitable type of cation comprises a cationic oxidizing agent represented by the formula:

$$Ox^{e+}$$

wherein $Ox^{e+}$ is a cationic oxidizing agent having a charge of e+, and e is an integer from 1 to 3.

Another suitable type of cation comprises an organometallic cation, such as, for example, $AlR'_2{}^+$, where $R'$ is a hydrocarbyl or substituted hydrocarbyl having from 1 to 100 nonhydrogen atoms, or $S-AlR'^+$, where S is a support material or other substrate having tethered to it an $AlR'^+$ group, where $R'$ is as previously defined.

Examples of cationic oxidizing agents include: ferrocenium, hydrocarbyl-substituted ferrocenium, $Ag^+$, and $Pb^{2+}$.

According to a further aspect of the present invention there is provided a nonsupported catalyst comprising the ionic compound (a), (b) a transition metal compound, and (c) an organometal compound wherein the metal is selected from the Groups 1–14 of the Periodic Table of the Elements. The nonsupported catalyst may be formed from soluble components (a), (b) and (c) and used in a diluent in which it is soluble, such as, for example, in a solution polymerization process, or it may be recovered as a solid in dry particulate form. In one aspect of this invention, the nonsupported solid catalysts are preferably dispersed in a diluent in which the solid catalyst is insoluble or sparingly soluble.

The present invention furthermore provides a supported solid catalyst comprising ionic compound (a), transition metal compound (b), organometal compound (c), and a support material (d). Suitable ionic compounds (a) have been described hereinabove.

Suitable transition metal compounds (b) for use in the present invention include any compound or complex of a metal of Groups 3–10 of the Periodic Table of the Elements capable of being activated to olefin insertion and polymerization when combined with components (a) and (c) and optionally (d) of the present invention. Examples include Group 10 transition metal diimine derivatives which are described in WO-96/23010.

Additional catalysts include derivatives of Group 3, 4, 5, or 6 or Lanthande metals which are in the +2, +3, or +4 formal oxidation state. Preferred compounds include metal complexes containing from 1 to 3 π-bonded anionic or neutral ligand groups, which may be cyclic or noncyclic delocalized π-bonded ligand groups. Exemplary of such π-bonded ligand groups are conjugated or nonconjugated, cyclic or noncyclic dienyl groups, allyl groups, boratabenzene groups, and arene groups. By the term "π-bonded" is meant that the ligand group is bonded to the transition metal by means of delocalized π electrons thereof.

Each atom in the delocalized π-bonded group may independently be substituted with a radical selected from the group consisting of hydrogen, halogen, hydrocarbyl, halohydrocarbyl, hydrocarbyl substituted metalloids, hydrocarbyloxy, dihydrocarbylamino, wherein the metalloid is selected from Group 14 of the Periodic Table of the Elements and hydrocarbyl radicals or hydrocarbyl-substituted metalloid radicals further substituted with a Group 15 or 16 heteroatom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, a hydrogenated fused ring system, or a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups. Such hydrocarbyl and hydrocarbyl-substituted organometalloid radicals may be further substituted with a Group 15 or 16 heteroatom containing moiety. Examples of Group 15 or 16 heteroatom containing moieties include amine, phosphine, ether or thioether moieties (see for example the compounds disclosed in WO-96/13529) or divalent derivatives thereof, for example amide, phosphide, ether or thioether groups bonded to the transition metal or Lanthande metal, and bonded to the hydrocarbyl group or to the hydrocarbyl substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted, $C_{1-10}$ hydrocarbyl-substituted silyl substituted, $C_{1-10}$ hydrocarbyl substituted germyl derivatives thereof, and divalent derivatives of the foregoing substituents. Preferred anionic delocalized π-bonded groups are cyclopentadienyl, pentamethylcyclopentadienyl, tetramethylcyclopentadienyl, tetramethylsilylcyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Heirberich, et al., in *Organometallics*, 14,1, 471–480 (1995). Preferred boratabenzenes correspond to the formula:

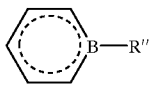

wherein R" is selected from the group consisting of hydrocarbyl, silyl, or germyl, said R" having up to 20 nonhydrogen atoms.

A suitable class of transition metal compounds useful in the present invention corresponds to the formula (V):

$$L_lMX_mX'_nX''_p, \text{ or a dimer thereof} \qquad (V)$$

wherein:

L is an anionic, delocalized, π-bonded group that is bound to M, containing up to 50 nonhydrogen atoms, optionally two L groups may be joined together forming a bridged structure, and further optionally one L may be bound to X;

M is a metal of Group 4 of the Periodic Table of the Elements in the +2, +3 or +4 formal oxidation state;

X is an optional, divalent substituent of up to 50 nonhydrogen atoms that together with L forms a metallocycle with M;

X' is an optional neutral ligand base having up to 20 nonhydrogen atoms:

X" each occurrence is a monovalent, anionic moiety having up to 40 nonhydrogen atoms, optionally, two X" groups may be covalently bound together forming a divalent dianionic moiety having both valences bound to M, or, optionally two X" groups may be covalently bound together to form a neutral, conjugated or nonconjugated diene that is π-bonded to M, or further optionally one or more X" and one or more X' groups may be bonded together thereby forming a moiety that is both covalently bound to M and coordinated thereto by means of Lewis base functionality;

l is 0, 1 or 2;

m is 0 or 1;

n is a number from 0 to 3;

p is an integer from 0 to 3; and the sum, l+m+p, is equal to the formal oxidation state of M, except when two X" groups together form a neutral conjugated or nonconjugated diene that is π-bonded to M, in which case the sum l+m is equal to the formal oxidation state of M.

Preferred complexes include those containing either one or two L groups. The latter complexes include those containing a bridging group linking the two L groups. Preferred bridging groups are those corresponding to the formula $(ER^*_2)_x$ wherein E is silicon, germanium, tin, or carbon, R* independently each occurrence is hydrogen or a group selected from silyl, hydrocarbyl, hydrocarbyloxy, and combinations thereof, said R* having up to 30 carbon or silicon atoms, and x is 1 to 8. Preferably, R* independently each occurrence is methyl, ethyl, propyl, benzyl, tert-butyl, phenyl, methoxy, ethoxy or phenoxy.

Examples of the complexes containing two L groups are compounds corresponding to the formula (VI) and (VII):

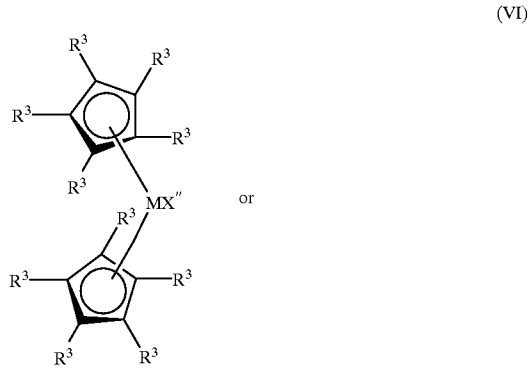

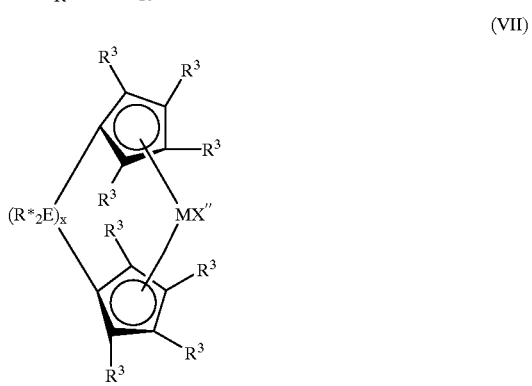

wherein:

M is titanium, zirconium or hafnium, preferably zirconium or hafnium, in the +2 or +4 formal oxidation state;

$R^3$ in each occurrence independently is selected from the group consisting of hydrogen, hydrocarbyl, silyl, germyl, cyano, halo and combinations thereof, said $R^3$ having tip to 20 nonhydrogen atoms, or adjacent $R^3$ groups together form a divalent derivative (that is, a hydrocarbadiyl, siladiyl or germadiyl group) thereby forming a fused ring system, and X" independently each occurrence is an anionic ligand group of up to 40 nonhydrogen atoms, or two X" groups together form a divalent anionic ligand group of up to 40 nonhydrogen atoms or together are a conjugated diene having from 4 to 30 nonhydrogen atoms forming a π-complex with M, whereupon M is in the +2 formal oxidation state, and R*, E and x are as previously defined for bridging groups $(ER^*_2)_x$.

The foregoing metal complexes are especially suited for the preparation of polymers having stereoregular molecular structure. In such capacity it is preferred that the complex possesses $C_s$ symmetry or possesses a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 100, 6255–6256 (1980). Examples of chiral structures include rac bis-indenyl complexes. Similar systems based on Ti(IV) or Zr(IV) were disclosed for preparation of isotactic olefin polymers in Wild et al., *J. Organomet. Chem.*, 232, 233–47, (1982).

Exemplary bridged ligands containing two π-bonded groups are: (dimethylsilyl-bis(cyclopentadienyl)), (dimethylsilyl-bis(methlcyclopentadienyl)), (dimethylsilyl-bis(ethylcyclopentadineyl)), (dimethylsilyl-bis)t-butylcyclopentadineyl)), (dimethylsilyl-bis (tetramethylcyclopentadienyl)), (dimethylsilyl-bis) indenyl)), dimethylsilyl-bis(tetrahydroindenyl)), dimethylsilyl-bis(fluorenyl)), dimethylsilyl-bis (tetrahydrofluorenyl)), dimethylsilyl-bis(2-methyl-4-phenylindenyl)), (dimethylsilyl-bis(2-methylindenyl)), dimethylsilylcyclopentadienyl-fluorenyl), (dimethylsilyl-cyclopentadienyl-octahydrofluorenyl), (dimethylsilyl-cyclopentadienyl-tetrahydrofluorenyl), (1,1,2,2-tetramethyl-1,2-disilyl-bis-cyclopentadienyl), (1,2-bis (cyclopentadienyl)ethane, and (isopropylidenecyclopentadienyl-fluorenyl).

Preferred X" groups in formula (VI) and (VII) are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention corresponds to the preceding formula (V)L$_1$MX$_m$X'$_n$X"$_p$, or a dimer thereof, wherein X is a divalent substituent of up to 50 nonhydrogen atoms that together with L forms a metallocycle with M.

Preferred divalent X substituents include groups containing up to 30 nonhydrogen atoms comprising at least one atom that is oxygen, sulfur, boron or a member of Group 14 of the Periodic Table of the Elements directly attached to the delocalized π-bonded group, and a different atom, selected from the group consisting of nitrogens phosphorus, oxygen or sulfur that is covalently bonded to M.

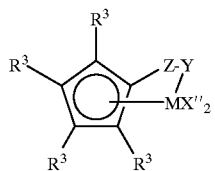

(VIII)

A preferred class of such Group 4 metal coordination complexes used according to the present invention corresponds to the formula (VIII):
wherein:
M is titanium or zirconium, preferably titanium in the +2, +3, or +4 formal oxidation state;
$R^3$ in each occurrence independently is selected from the group consisting of hydrogen, hydrocarbyl, silyl, germyl, cyano, halo, hydrocarbyloxy, dihydrocarbylamino, and combinations thereof, said $R^3$ having up to 20 nonhydrogen atoms, or adjacent $R^3$ groups together form a divalent derivative (that is, a hydrocarbadiyl, siladiyl or germadiyl group) thereby forming a fused ring system;
each X" in formula (VIII) is a hydride, halide, hydrocarbyl, hydrocarbyloxy or silyl group, said group having up to 20 nonhydrogen atoms, or two X" groups together form a neutral $C_{5-30}$ conjugated diene or a divalent derivative thereof;
Y is —O—, —S—, —NR*—, —PR*—, —NR*$_2$ or —PR*$_2$; and
Z is SiR*$_2$, CR*$_2$, SiR*$_2$SiR*$_2$, CR*$_2$CR*$_2$, CR*=CR*, CR*$_2$SiR*$_2$, or GeR*$_2$, wherein R* is as previously defined.

According to the present invention there are provided metal complexes corresponding to the formula I:

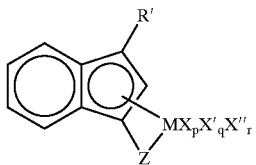

(I)

where M is titanium, zirconium or hafnium in the +2, +3 or +4 formal oxidation state;
R' is an aryl ligand or a halo-, silyl-, alkyl-, cycloalkyl-, dihydrocarbylamino-, hydrocarbyloxy-, or hydrocarbyleneamino-, substituted derivative thereof, said R' having, from 6 to 40 nonhydrogen atoms;
Z is a divalent moiety, or a moiety comprising one σ-bond and a neutral two electron pair able to form a coordinate-covalent bond to M, said Z comprising, boron, or a member of Group 14 of the Periodic Table of the Elements, and also comprising nitrogen, phosphorus, sulfur or oxygen;
X is a monovalent anionic ligand group having up to 60 atoms exclusive of the class of ligands that are cyclic, delocalized, π-bound ligand groups;
X' independently each occurrence is a neutral Lewis base ligating compound having up to 20 atoms;
X" is a divalent anionic ligand group having up to 60 atoms;
p is zero, 1, 2, or 3;
q is zero, 1 or 2; and
r is zero or 1.

Another class of preferred metal complexes for use in the present invention corresponding to the formula:

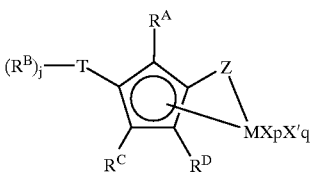

where M is a metal from one of Groups 3 to 13 of the Periodic Table of the Elements, the lanthanides or actinides, which is in the +2, +3 or +4 formal oxidation state and which is π-bonded to one cyclopentadienyl group (Cp) which is a cyclic, delocalized, π-bound ligand group having 5 substituents: $R^A$; $(R^B)_j$—T where j is zero, 1 or 2; $R^C$; $R^D$ and Z; where $R^A$, $R^B$, $R^C$ and $R^D$ are R groups; and where T is a heteroatom which is covalently bonded to the Cp ring, and to $R^B$ when j is 1 or 2, and when j is 0, T is F, Cl, Br, or I; when j is 1, T is O or S, or N or P and $R^B$ has a double bond to T; when j is 2, T is N or P; and where $R^B$ independently each occurrence is hydrogen, or, is a group having from 1 to 80 nonhydrogen atoms which is hydrocarbyl, hydrocarbylsilyl, halo-substituted hydrocarbyl, hydrocarbyloxy-substituted hydrocarbyl, hydrocarbylamino-substituted hydrocarbyl, hydrocarbylsilyhydrocarbyl, hydrocarbylamino, di(hydrocarbyl)amino, hydrocarbyloxy, each $R^B$ optionally being substituted with one or more groups which independently each occurrence is hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilyhydrocarbyl having from 1 to 20 nonhydrogen atoms, or a noninterfering group having from 1 to 20 nonhydrogen atoms; and each of $R^A$, $R^C$ and $R^D$ is hydrogen, or is a group having from 1 to 80 nonhydrogen atoms which is hydrocarbyl, halo-substituted hydrocarbyl, hydrocarbyloxy-substituted hydrocarbyl, hydrocarbylamino-substituted hydrocarbyl, hydrocarbylsilyl, hydrocarbylsilylhydrocarbyl, each $R^A$, $R^C$ or $R^D$ optionally being substituted with one or more groups which independently each occurrence is hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilylihydrocarbyl having from 1 to 20 nonhydrogen atoms, or a noninterfering group having from 1 to 20 nonhydrogen atoms: or, optionally, two or more of $R^A$, $R^B$, $R^C$ and $R^D$ are covalently linked with each other to form one or more fused rings or ring systems having from 1 to 80 nonhydrogen atoms for each R group, the one or more fused rings or ring systems being unsubstituted or substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilylhydrocarbyl having from 1 to 20 nonhydrogen atoms, or a noninterfering group having from 1 to 20 nonhydrogen atoms;

Z is a divalent moiety bound to both Cp and M via σ-bonds, where Z comprises boron, or a member of Group 14 of the Periodic Table of the Elements, and also comprises nitrogen, phosphorus, sulfur or oxygen;

X is an anionic or dianionic ligand group having up to 60 atoms exclusive of the class of ligands that are cyclic, delocalized, π-bound ligand groups;

X' independently each occurrence is a neutral Lewis base ligating compound having up to 20 atoms;

p is zero, 1 or 2, and is two less than the formal oxidation state of M, when X is an anionic ligand; when X is a dianionic ligand group, p is 1; and q is zero, 1 or 2.

Another class of preferred metal complexes for use in the present invention corresponding to the formula:

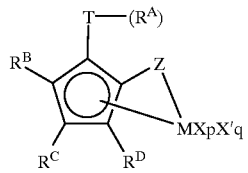

where M is a metal from one of Groups is 3 to 13 of the Periodic Table of the Elements, the lanthanides or actinides, which is in the +2, +3 or +4 formal oxidation state and which is π-bonded to one cyclopentadienyl group (Cp) which is a cyclic, delocalized, π-bound ligand group having 5 substituents: $(R^A)_j$—T where j is zero, 1 or 2, where $R^A$, $R^B$, $R^C$ and $R^D$ are R groups: and where T is a heteroatom which is covalently bonded to the Cp ring, and to $R^A$ when j is 1 or 2, and when j is 0, T is F, Cl, Br, or I; when j is 1, T is O or S, or N or P and $R^A$ has a double bond to T; when j is 2, T is N or P; and where $R^A$ independently each occurrence is hydrogen, or, is a group having from 1 to 80 nonhydrogen atoms which is hydrocarbyl, hydrocarbylsilyl, halo-substituted hydrocarbyl, hydrocarbyloxy-substituted hydrocarbyl, hydrocarbylamino-substituted hydrocarbyl, hydrocarbylsilylhydrocarbyl, hydrocarbylamino, di(hydrocarbyl)amino, hydrocarbyloxy, each $R^A$ optionally being, substituted with one or more groups which independently each occurrence is hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilylhydrocarbyl having from 1 to 20 nonhydrogen atoms, or a noninterfering group having from 1 to 20 nonhydrogen atoms; and each of $R^B$, $R^C$ and $R^D$ is hydrogen, or is a group having from 1 to 80 nonhydrogen atoms which is hydrocarbyl, halo-substituted hydrocarbyl, hydrocarbyloxy-substituted hydrocarbyl, hydrocarbylamino-substituted hydrocarbyl, hydrocarbylsilyl, hydrocarbylsilylhydrocarbyl, each $R^B$, $R^C$ or $R^D$ optionally being substituted with one or more groups which independently each occurrence is hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilylhydrocarbyl having from 1 to 20 nonhydrogen atoms, or a noninterfering group having from 1 to 20 nonhydrogen atoms; or, optionally, two or more of $R^A$, $R^B$, $R^C$ and $R^D$ are covalently linked with each other to form one or more fused rings or ring systems having from 1 to 80 nonhydrogen atoms for each R group, the one or more fused rings or ring systems being unsubstituted or substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilylhydrocarbyl having, from 1 to 20 nonhydrogen atoms, or a noninterfering group having from 1 to 20) nonhydrogen atoms;

Z is a divalent moiety bound to both Cp and M via σ-bonds, where Z comprises boron, or a member of Group 14 of the Periodic Table of the Elements, and also comprises nitrogen, phosphorus, sulfur or oxygen;

X is an anionic or dianionic ligand group having up to 60 atoms exclusive of the class of ligands that are cyclic, delocalized, π-bound ligand groups;

X' independently each occurrence is a neutral Lewis base ligating compound having up to 20 atoms;

p is zero, 1 or 2, and is two less than the formal oxidation state of M, when X is an anionic ligand; when X is a dianionic ligand group, p is 1; and q is zero, 1 or 2.

Specific examples of some of the transition metal compounds of the types described above can be found in EP-0 129 368; EP-0 277 004; EP-0 416 815; WO-93/19104; WO-95/00526; WO-96/00734; WO-96/04290; WO-96/08498; while others, especially constrained geometry metal complexes and methods for their preparation, are disclosed in U.S. application Ser. No. 545,403, filed Jul. 3, 1990; U.S. application Ser. No. 547,718, filed Jul. 3, 1990 ABN (EP-A-468,651); U.S. application Ser. No. 702,475, filed May 20, 1991 ABN (EP-A-514,828); U.S. application Ser. No. 876,268, filed May 1, 1992, U.S. Pat. No. 5,721,185 (EP-A-520,732); and U.S. application Ser. No. 8.003, filed Jan. 21, 1993 U.S. Pat. No. 5,374,696); as well as U.S. Pat. Nos. 5,055,438; 5,057,475; 5,096,867; 5,064,802; 5,132,380; WO-96/28480; WO-97/15583; U.S. application Ser. No. 08/689,163 filed Aug. 7, 1996 ABN; U.S. application Ser. No. 08/818,530 filed Mar. 14, 1997 U.S. Pat. No. 5,919,983; WO-97/35893: U.S. application Ser. No. 60/017,147 filed May 17, 1996; PCT Application No. PCT/US97/08206 filed May 16, 1997; PCT Application No. PCT/US97/08466 filed May 16, 1997; U.S. application Ser. No. 60/034,819 filed Dec. 19, 1996; U.S. application Ser. No. 60/023,768 filed Aug. 8, 1996; PCT Application No. PCT/US97/13170 filed Jul. 28, 1997; PCT Application No. PCT/US97/13171 filed Jul. 28, 1997; and U.S. application Ser. No. 08/768,518 filed Dec. 18, 1996 U.S. Pat. No. 5,783,512. Also to be found therein are teachings related to various olefin polymerization processes and the products produced in those processes which are relevant to the processes described herein for the use of various aspects of this invention. The teachings of all of the foregoing patents and the corresponding U.S., EP, and WO patent applications are hereby incorporated by reference.

Suitable organometal or metalloid compounds (c) for use in the present invention are those comprising a metal or metalloid of Groups 1–14. In one aspect component (c) contains at least one substituent selected from hydride, hydrocarbyl groups, trihydrocarbyl silyl groups, and trihydrocarbyl germyl groups. It is desirable that this at least one substituent be capable of reacting with the moiety having all active hydrogen of the anion (a)(2)of the ionic compound. Additional substituents preferably comprise one or more substituents selected from hydride, halide, hydrocarbyloxide, dihydrocarbylamide hydrocarbyl groups, trihydrocarbyl substituted silyl groups, trihydiocarbyl substituted germyl groups, and hydrocarbyl-, trihydrocarbyl silyl- or trihydrocarbyl germyl-substituted metalloid groups. Desirable organometal or metalloid compound (c) corresponds to the formula:

wherein $M^o$ is a metal or metalloid selected from Groups 1–14 of the Periodic Table of the Elements, $R^C$ independently each occurrence is hydrogen or a group having from 1 to 80 nonhydrogen atoms which is hydrocarbyl, hydrocarbylsilyl, trihydrocarbylsilyl, trihydrocarbylgermyl or hydrocarbylsilylhydrocarbyl;

$X^a$ is a noninterfering group having from 1 to 100 nonhydrogen atoms which is halo-substituted hydrocarbyl, hydrocarbylamino-substituted hydrocarbyl, hydrocarbyloxy-substituted hydrocarbyl, hydrocarbylamino, di(hydrocarbyl)amino, hydrocarbyloxy or halide;

x is a nonzero integer which may range from 1 to an integer equal to the valence of $M^o$;

y is zero or a nonzero integer which may range from 1 to an integer equal to 1 less than the valence of $M^o$; and x+y equals the valence of $M^o$.

Preferred organometal compounds (c) are those where $M^o$ is selected from Groups 2, 12, 13 or 14 of the Periodic Table of Elements,more desirably, Mg, Zn, B, Al, Ga, Si, Ge, Sn, or Pb, with aluminum and magnesium being preferred and aluminum being the most preferred.

Examples of organometal compounds (c) include organolithium, organosodium, organomagnesium, organoscandium, organotitanium, organovanadium, organochromium, organomaganese, organoiron, organocobalt, organonickel, organocopper, organosilver, organozinc, organoboron, organoaluminum, organosilicon, organogermanium, organotin, and organolead compounds, and mixtures thereof.

Examples of preferred organometal compounds (c) include organlithium, organomagnesium, organozinc, organoboron, organoaluminum, organosilicon, organogermanium, organotin, and organolead compounds, mixtures thereof. More preferred examples are compounds represented by the following formulae: $MgR^1{}_2$, $ZnR^1{}_2$, $BR^1{}_xR^2{}_y$, $AlR^1{}_xR^2{}_y$, wherein $R^1$ independently each occurrence is hydride, a hydrocarbyl radical, a trihydrocarbyl silyl radical, a trihydrocarbyl germyl radical, or a trihydrocarbyl-, trihydrocarbyl silyl- or trihydrocarbyl germyl-substituted metalloid radical, $R^2$ independently is the same as $R^1$, x is 2 or 3, y is 0 or 1 and the sum of x and y is 3, and mixtures thereof. Examples of suitable hydrocarbyl moieties are those having from 1 to 20 carbon atoms in the hydrocarbyl portion thereof, such as alkyl, aryl, alkaryl, or aralkyl. Preferred radicals include methyl, ethyl, n- or i-propyl. n-, s- or t-butyl, phenyl, and benzyl. Preferred components (c) are the aluminum and magnesium compounds, and especially the aluminum compounds. Preferably, the aluminum component is an aluminum compounds of the formula $AlR^1{}_x$ wherein $R^1$ in each occurrence independently is hydride or a hydrocarbyl radical having from 1 to 20 carbon atoms, and x is 3. Suitable trihydrocarbyl aluminum compounds are trialkyl or triaryl aluminum compounds wherein each alkyl or aryl group has from 1 to 10 carbon atoms, or mixtures thereof, and preferably trialkyl aluminum compounds such as trimethyl, triethyl, tri-isobutyl aluminum.

Alumoxanes (also referred to as aluminoxanes) may also be used as component (c), or (c) may be a mixture of one of the compounds mentioned in the preceding paragraphs and an alumoxane. Alumoxanes are oligomeric or polymeric aluminum oxy compounds containing chains of alternating aluminum and oxygen atoms, whereby the aluminum carries a substituent, preferably an alkyl croup. The structure of alumoxane is believed to be represented by the following general formulae $(-Al(R)-O)_m$, for a cyclic alumoxane, and $R_2Al-O(-Al(R)-O)_m-AlR_2$, for a linear compounds wherein R independently in each occurrence is a $C_1-C_{10}$ hydrocabyl, preferably alkyl, or halide and m is an integer ranging from 1 to about 50, preferably at least about 4. Alumoxanes are typically the reaction products of water and an aluminum alkyl, which in addition to an alkyl group may contain halide or alkoxide groups. Reacting several different aluminum alkyl compounds, such as, for example, trimethyl aluminum and tri-isobutyl aluminum, with water yields so-called modified or mixed alumoxanes. Preferred alumoxanes are methylalumoxane and methylalumoxane modified with minor amounts of other lower alkyl groups such as isobutyl, Alumoxanes generally contain minor to substantial amounts of starting aluminum alkyl compound.

The way in which the alumoxane is prepared is not critical. When prepared by the reaction between water and aluminum alkyl, the water may be combined with the aluminum alkyl in various forms, Such as liquid, vapor, of solid, for example in the form of crystallization water. Particular techniques for the preparation of alumoxane type compounds by contacting an aluminum alkyl compound with an inorganic salt containing, water of crystallization are disclosed in U.S. Pat. No. 4,542,199. In a particular preferred embodiment an aluminum alkyl compound is contacted with a regeneratable water-containing substance such as hydrated alumina, silica or1 other substance. This is disclosed in European Patent Application No. 338,044.

According to a further aspect the invention provides a supported solid catalyst comprising, (a), (b), and (c) as described hereinbefore, as well as (d) a support material.

Suitable support materials (d), also referred to as carriers or carrier materials, which may optionally be used in the present invention include those support materials which are typically used in the art of supported catalysts, and more in particular the art of supported olefin addition polymerization supported catalysts. Examples include porous resinous materials, for example, polyolefins such as polyethylenes and polypropylenes or copolymers of styrene-divinylbenzene, and solid inorganic oxides including oxides of Group 2, 3, 4, 13, or 14 metals, such as silica, alumina, magnesium oxide, titanium oxide, thorium oxide, as well as mixed oxides of silica. Suitable mixed oxides of silica include those of silica and one or more Group 2 or 13 metal oxides, such as silica-magnesia or silica-alumina mixed oxides. Silica, alumina, and mixed oxides of silica and one or more Group 2 or, 13 metal oxides are preferred support materials. Preferred examples of such mixed oxides are the silica-aluminas. The most preferred support material is silica. The shape of the silica particles is not critical and the silica may be in granular, spherical, agglomerated, fumed or other form.

Support materials suitable for the present invention preferably have a surface area as determined by nitrogen porosimetry using the B.E.T. method from 10 to about 1000 $m^2/g$, and preferably from about 100 to 600 $m^2/g$. The pore volume of the support, as determined by nitrogen adsorption, is typically up to 5 $cm^3/g$, advantageously between 0.1 and 3 $cm^3/g$, preferably from about 0.2 to 2 $cm^3/g$. The average particle size is not critical but typically is from 0.5 to 500 $\mu m$, preferably from 1 to 200 $\mu m$, more preferably to 100 $\mu m$.

Preferred supports for use in the present invention include highly porous silicas, aluminas, aluminosilicates, and mixtures thereof. The most preferred support material is silica. The support material may be in granular, agglomerated, pelletized, or any other physical form. Suitable materials include, but are not limited to, silicas available from Grace Davison (division of W. R. Grace & Co.) under the designations SD 3216.30, Davison Syloid™245, Davison 948 and Davison 952, and from Crosfield under the designation ES70, and from Degussa AG under the designation Acrosil™812; and aluminas available from Akzo Chemicals Inc. under the designation Ketzen™ Grade B.

The support material may be subjected to a heat treatment and/or chemical treatment to reduce the water content or the hydroxyl content of the support material. Both dehydrated support materials and support materials containing small amounts of water can be used. Typical, chemical dehydration or dehydroxylation agents are reactive metal hydrides, alkyls and halides such as aluminum alkyls, alkyl silicon halides and the like. Prior to its use, the support material can be subjected to a thermal treatment at 100° C. to 1000° C., preferably at about 200° C. to about 850° C. in an inert atmosphere or under reduced pressure. Typically, this treatment is carried out for about 10 minutes to about 72 hours, preferably from about 0.5 hours to 24 hours.

The support material, optionally thermally treated, may preferably be combined with a further organometal metalloid compound, more preferably an organoaluminum compound, most preferably a trialkylaluminum compound in a suitable diluent or solvent, preferably one in which the organometal compound is soluble. Typical solvents are hydrocarbon solvents having from 5 to 12 carbon atoms, preferably aromatic solvents such as toluene and xylenes, or aliphatic solvents of 6 to 10 carbon atoms, such as hexane, heptane, octane, nonane, decane, and isomers thereof, cycloaliphatic solvents of 6 to 12 carbon atoms such as cyclohexane, or mixtures of any of these.

The support material is combined with the organometal compound at a temperature of −20° C. to 150° C., preferably at 20° C. to 100° C. The contact time is not critical and can vary from 5 minutes to 72 hours, and is preferably from 0.5 hours to 36 hours. Agitation is preferably applied.

An alternative pretreatment of the support material involves a treatment with alumoxane. The alumoxane may be contacted with the support material in the manner described above of the alumoxane may be generated in situ on the support material by contacting an alkylaluminum, preferably trialkylaluminum compound, with a support material containing water.

The pretreated support material is preferably recovered prior to its further use.

Pretreated support material do not contain the tethering groups, such as, for example, surface hydroxyl groups, which are typically found in various support materials, especially silicas and silica containing support materials. Pretreated support materials may contain terminal residues of a material used for pretreatment, such as, for example, an alumoxane residue or the residue of a trialkylaluminum compound, such as —AlR2. Certain of these residues, in particular an alumoxane residue or the residue of a trialkylaluminum compound, are capable of reacting with the moiety having an active hydrogen of the anion (a)(2) of the ionic compound. However, if a pretreated silica is used in a process, and at some point in the process a compound which is the reaction product of (a) an ionic compound and (c) an organometal or metalloid compound, or a substantially inactive catalyst precursor are brought into contact, reaction to form a covalent bond with tethering to the support is not possible, since all potentially reactive groups which could enter into a reaction resulting in tethering have been blocked or capped.

In various aspects of this invention where a support material is employed, including catalyst components and catalysts, as well as corresponding aspects which are nonsupported, whether as homogeneous solutions, solids or dispersions, an alternative expression of each of those aspects is one that is essentially free of alumoxane.

According to the present invention, the ionic compound (a) can be formed into a dispersion of solid particles (a) by a controlled precipitation. This dispersion can he used as such in the preparation of a solid catalyst suitable for addition polymerization processes, thereby maintaining the dispersed nature. A range of suitable particle sizes for the solid dispersed catalyst can be obtained by selecting the solvents and nonsolvents, temperature conditions and the specific catalyst components. No intermediate recovery or separation steps are required and the final solid catalyst, preferably still hi dispersed form, may be employed as such in an addition polymerization process. Alternatively, the particulate solid (a) and the solid catalyst, and any solid intermediate product, can be recovered from the diluent in which it is dispersed by removing the liquid or nonsolvent employing techniques such as filtration, vacuum drying, spray drying, and combinations thereof. Prior to its use, the particulate solid (a), the solid catalyst, and any solid intermediate product, may be redispersed in a suitable liquid diluent.

The catalyst component dispersion of the present invention can be prepared by converting a solution of the ionic compound (a), in a diluent (solvent) in which (a) is soluble, into a dispersion comprising component (a) in solid form.

It may be desirable to use a method wherein the converting is done in the presence of (b) a transition metal compound and wherein the catalyst component is a substantially inactive catalyst precursor; or wherein the converting, is clone in the presence of (c) an organometal or metalloid compound wherein the metal or metalloid is selected from the Groups 1–14 of the Periodic Table of the Elements and the catalyst component is a reaction product of (a) and (c), or, alternatively, it may be desirable to employ the method such that the catalyst component excludes (b) a transition metal compound, excludes (c) an organometal or metalloid compound wherein the metal or metalloid is selected from the Groups 1–14 of the Periodic Table of the Elements, or excludes both (b) and (c).

A solution of ionic compound (a) in a diluent can be obtained by using an appropriate solvent in which (a) is soluble. The diluent in which (a) is dissolved is not critical. Preferably, the diluent is compatible with the other catalyst components and under polymerization conditions, so that it does not need to be removed prior to its further use. Suitable solvents for (a) include aromatic hydrocarbons, such as toluene, benzene, ethylbenzene, propylbenzene, butylbenzene, xylenes, chlorobenzene, and the like.

When a solvent is used in which (a) is not sufficiently soluble, or in order to assist in or speed up dissolution of (a), heating may be applied or solubilizing agents may be used, or a combination of both. The solubilizing agent to be used is compatible with the catalyst components, in a sense that it does not adversely affect the beneficial properties of the catalyst. Heating is preferably done at temperatures not higher than the decomposition temperature of (a). During the dissolution of (a) stirring is advantageously applied.

Preferably, the solution of (a) contains from 0.0001 to 100 mole of (a) per liter, more preferably from 0.001 to 10 mole per liter. Any nondissolved (a) is preferably removed by, for example, filtration techniques, prior to further using the solution of (a).

The solution of (a) is then converted into a dispersion comprising (a) in solid form. The conversion of the solution of (a) to a dispersion of (a) can be carried out, for example, by a process wherein the dispersion comprising component (a) is generated by cooling a solution of (a) in a diluent in which (a) is soluble, by contacting a solution of (a) in a diluent in which (a) is soluble with a diluent in which (a) is insoluble or sparingly soluble, by evaporating diluent from a solution of (a), by adding one or more precipitating agents to a solution of (a), or a combination of two or more of these techniques, to achieve a controlled precipitation or solidification such that a dispersion of (a) is formed. It will be clear to a person skilled in the art that the distinction between a solvent and a nonsolvent for a particular ionic compound (a) will primarily depend on the nature of the particular compound (a), on the temperature, and relative amount of (a) to be dissolved. For a given ionic compound (a), the skilled person can easily determine what solvent and temperature conditions are to be used to obtain a solution of the desired concentration. On the other hand, given the solution of (a), the skilled person can easily determine the conditions and means to obtain the dispersion of (a) having the desired solids concentration.

When precipitating agents are used, they are preferably compatible with the catalyst components, such that the beneficial properties of the catalyst are not adversely affected.

The nonsolvent employed for generating the dispersion of (a) is not critical. Preferably, the nonsolvent is compatible with the other catalyst components and under polymerization conditions, so that it does not need to be removed prior to further use. Preferred nonsolvents are, for example, pentane, hexane, heptane decane, dodecane, kerosene, and higher aliphatic hydrocarbons of up to 30 carbon atoms.

The dispersion comprising component (a) is preferably generated by contacting a solution of (a) in a diluent in which (a) is soluble with a diluent in which (a) is insoluble or sparingly soluble. The diluent in which (a) is soluble is preferably selected from the group consisting of toluene, benzene, and xylenes, and the diluent in which (a) is insoluble or sparingly soluble is preferably selected from the group consisting of pentane, hexane, heptane, and octane.

In contacting the solution of (a) with the nonsolvent, the amount of nonsolvent is usually 10 to 10,000 parts by weight, preferably 100 to 1,000 parts by weight per 100 parts by weight of the solution of (a). The contacting temperature is usually from −100 to 300° C., preferably from −50 to 130° C., and most preferably from 10 to 110° C.

When the solvent, in which (a) is dissolved, needs to be removed after contacting with the nonsolvent, the solvent is preferably selected so that it has a lower boiling point than that of the nonsolvent. The solvent can then be easily removed by heating the dispersion or by applying reduced pressure.

The solid catalysts, either supported or nonsupported, according to the present invention can be prepared by combining, in any order, components (a), (b), (c), and optionally (d) in case of a supported catalyst, wherein during at least one step in the preparation of the solid catalyst, component (a) dissolved in a diluent in which (a) is soluble, optionally in the presence of one or more of components (b), (c), and (d) or the contact product of (a) with one or more of (b), (c), and (d), is converted into solid form, optionally followed by recovering the solid catalyst. After this step the other components (b), (c) and optionally (d), to the extent they have not been added before, are contacted with (a) in solid form, preferably dispersed in solid form.

According to an aspect of this invention, the methodology of which is similar to that described above for the preparation of dispersions of catalyst components, it is desirable that during the at least one step in the preparation of the solid catalyst, a dispersion comprising component (a) in solid form is generated by cooling a solution of (a) in a diluent in which (a) is soluble, by contacting a solution of (a) in a diluent in which (a) is soluble with a diluent in which (a) is insoluble or sparingly soluble, by evaporating diluent from a solution of (a), by adding one or mole precipitating agents to a solution of (a), or a combination of two or more of these techniques.

According to a preferred embodiment for the preparation of the nonsupported or supported solid catalyst, during the at least one step in the preparation of the solid catalyst, a dispersion comprising component (a) in solid form is generated by contacting a solution of (a) in a diluent in which (a) is soluble, optionally in the presence of one or more of components (b), (c), and (d) or the contact product of (a) with one or more of (b), (c), and (d), with a diluent in which (a) is insoluble or sparingly soluble.

In all the process steps subsequent to the dispersion formation step, it is preferred not to use temperature conditions or types or quantities of solvents that would redissolve compound (a). The methods that can be used to generate the dispersion of (a) are essentially those which have been described above in relation to the formation of the catalyst component dispersion.

In the method for preparing the nonsupported or supported solid catalyst, the dispersion comprising component (a) can be formed first whereupon the other components (b), (c), and optionally (d) can be combined in arbitrary order. Further, the dispersion comprising component (a) can be formed in the presence of one or more of the other components (b), (c) and optionally (d). Exemplary embodiments are given below.

In one embodiment for preparing the nonsupported or supported solid catalyst, the dispersion comprising component (a) is first contacted with component (b) and the resulting product is subsequently contacted with component (c). Component (b) is preferably employed dissolved in a suitable solvent, such as a hydrocarbon solvent, advantageously a $C_{5-10}$ aliphatic or cycloaliphatic hydrocarbon or a $C_{6-10}$ aromatic hydrocarbon. The contact temperature is not critical provided it is below the decomposition temperature of the transition metal. Component (c) can be used in a neat form, that is, as is, or dissolved in a hydrocarbon solvent, which may be similar to the one used for dissolving component (b).

In a further embodiment for preparing the nonsupported or supported solid catalyst, components (b) and (c) are first contacted, preferably in a suitable solvent, and then contacting the resulting product with the dispersion comprising component (a). The solvent or solvents used for contacting (b) and (c) are of such nature or are used in such quantities, or a combination thereof, that when the resulting product is contacted with the dispersion comprising (a), component (a) is not substantially redissolved.

In some of the methods of preparing a supported solid catalyst, including the precipitation methods described above, the manner in which component (d) is added is not critical. Component (d) can he added during one of the steps in the preparation of the solid catalyst. The support material (d) can be added after the components (a), (b), and (c) have been combined with each other, or (d) can be combined with at least one of the components prior to combining the resulting product with the remaining component or components.

According to a preferred embodiment for the preparation of a supported solid catalyst, component (a) dissolved in a solvent is first combined with component (d), whereupon a dispersion of (a) is generated in the manner as described above in relation to the generation of the dispersion of (a). The combining of component (d) with the solution of component (a) may be carried out while forming a slurry, that is, using an excess amount of liquid, or alternatively, only so much of the solution of component (a) is used that no slurry is formed. Advantageously in the latter situation, the volume of the solution of component (a) does not exceed substantially, and is preferably about equal to, the pore volume of component (d). After this contacting step, component (a) is converted into solid form, preferably by combining the contact product of (a) and (d) with a diluent in which (a) is insoluble or sparingly soluble. The amount of solids relative to the amount of nonsolvent is not critical but typically is from 0.001 to 50 weight percent.

When component (d) is contacted with a solution of (a), (d) is preferably used after it has been pretreated to remove substantially all water and surface hydroxyl groups, and especially by treatment with an aluminumalkyl, more preferably with an aluminumtrialkyl compound. It is advantageous to contact the solution of (a) with component (c), preferably with one molar equivalent of (c), prior to contacting the same with component (d). A highly preferred support material for use in these embodiments is pretreated silica.

Typical, yet not critical, temperatures for any of the steps except the dispersion formation step are −50 to 150° C. Preferably, each of the contacting steps is carried out while stirring or agitating. All steps in the present process should be conducted in the absence of oxygen and moisture.

In an alternative method for the preparation of solid supported catalysts, it is desirable that the support material used is a pretreated support material with a pore volume of from 0.1 to 5 $cm^3/g$ and in the supported catalyst the anion (a)(2) is not chemically bonded to the support (d), and wherein the volume of the solution of (a), optionally in the presence of one or both of (b) and (c), is from 20 volume percent to 200 volume percent of the total pore volume of the support material used. Preferred embodiments are those wherein the volume of the solution is from 70 (volume percent to 130 volume percent of the total pore volume of the support material used, or wherein the volume of the solution is substantially equal to the total pore volume of the support material used. Some aspects of this method may be similar to various aspects of processes for the preparation of supported catalyst, variously referred to as incipient impregnation or incipient wetness techniques, as disclosed in U.S. Pat. Nos. 5.602,067; 5,625,015; and PCT applications WO-95/12622; WO-96/23005; WO-96/16093; WO-97/02297; and WO-97/24375, all of which are hereby incorporated by reference.

In alternative aspects of this embodiment, as mentioned in the two paragraphs immediately above, it may be desirable that the solution of (a) is produced in the presence of (b), or in the presence of (c), or in the presence of (b) and (c).

Generally, in this aspect it is desirable that the solid catalyst is produced by adding the solution of (a), optionally containing one or both of (b) and (c), to substantially dry pretreated support material, followed by removal of the diluent.

In another alternative for the preparation of the supported catalyst, it is desirable that the support material used is a pretreated support material with a pore volume of from 0.1 to 5 cm$^3$/g and in the supported catalyst the anion (a)(2) is not chemically bonded to the support (d), and wherein the volume of the solution of (a), optionally in the presence of one or both of (b) and (c), is greater than 200 volume percent of the total pore volume of the support material used. In alternative aspects of this embodiment, it may be desirable that the solution of (a) is produced in the presence of (b), or in the presence of (c), or in the presence of (b) and (c). In this aspect it may be desirable that the solid catalyst is produced by adding the solution of (a), optionally containing one or both (b) and (c), to substantially dry pretreated support material, followed by removal of the diluent, or it may be added to a slurry of (d) in a diluent, followed by removal of the diluent.

The nonsupported or supported solid catalyst may be stored or shipped in free flowing form under inert conditions after removal of the solvent.

The combining of components (a) and (b) in equimolar amounts does not result in a catalyst composition that has substantial activity in addition polymerization processes. Upon combining this composition with component (c) an active catalyst composition is surprisingly formed. Therefore, a further embodiment provides a method for activating a substantially inactive catalyst precursor to form a catalyst suitable for addition polymerization wherein a substantially inactive catalyst precursor comprising an ionic compound (a) and a transition metal compound (b) and, optionally, component (d), is contacted with organometal compound (c) to form an active catalyst. In one aspect, preferably, the substantially inactive catalyst precursor is in a solid form, either supported or nonsupported, more preferably dispersed in a diluent, while in an alternative aspect wherein no support is used all the materials are used in solution form and the activation process produced a homogenous solution of a catalyst suitable for solution polymerization.

Preferably, according to this activating method, a dispersion of a nonsupported or supported solid substantially inactive catalyst precursor, comprising (a),(b) and optionally (d), and the organometal compound (c) are each separately added, preferably directly, into an addition polymerization reactor containing addition polymerizable monomer or monomers, preferably under addition polymerizable conditions. The catalyst components can be added separately to the reactor or to specific locations in the reactor which enables the catalyst to be activated only in the reactor or in a specific location in the reactor, which offers a more controllable polymerization reaction. This is especially advantageous where the addition polymerization reactor is operated under slurry phase or gas phase polymerization conditions.

The relative amounts of the components to be used in the compositions and processes of the present invention will now be described. The relative amount of ionic compound (a) to gramatoms of transition metal in compound (b), is not critical but generally is in the range from 0.1 to 500 mole of (a) per gramatoms of (b). Preferably, 0.5 to 100 mole of (a) per gramatoms of (b) is used, most preferably from about 1 to 3 mole of (a) per gramatoms of (b).

The ratio between organometal compound (c) and the ionic compound (a) is not critical, but generally lies within the range of 0.05 to 1,000 mole of (c) per mole of (a). Preferably, the ratio is from 0.5 to 100 mole (c) per mole (a), most preferably from about 1 to 50 mole (c) per mole (a).

The amount of optional component (d) to be used in the present invention is also not critical, however, typical values range from 0.1 $\mu$mol to 2 mmol of ionic compound (a) per gram of support material. Preferably, from 10 to 1,000 $\mu$mol of ionic compound (a) is used per gram of support material.

The solid catalyst can be used as such or after being subjected to prepolymerization. The prepolymerization can be carried out by any known methods such as by bringing a small amount of one or more polymerizable monomers into contact with the solid catalyst. The monomers which can be used in the prepolymerization are not particularly limited and include the olefins and diolefins mentioned hereinafter. It is preferable to use for the prepolymerization the same monomer as used in the subsequent polymerization. The prepolymerization temperature may usually range from –20° C. to 100° C., preferably from –10 to 70° C. more preferably from 0 to 50° C.

The prepolymerization may be carried out batchwise or continuously under atmospheric pressure or elevated pressures. The prepolymerization may be carried out in the presence of a molecular weight controlling agent such as hydrogen. The prepolymerization is carried out in the absence or presence of a solvent or diluent. When a solvent or diluent is used it is preferably an inert hydrocarbon, such as the ones described hereinafter with respect to the polymerization process. Preferably the solvent or diluent used does not substantially redissolve the solid catalyst comprising ionic compound (a). The prepolymerization is typically carried out to form a prepolymerized catalyst, that is polymer is formed on the solid catalyst particles, having from 0.1 to 100 g of polymer per 1 g of solid catalyst, preferably from 1 to 10 g of polymer per g of solid catalyst. Typical particle sizes of prepolymerized catalysts are in the range of 1 to 200 $\mu$m, preferably in the range from 10 to 100 $\mu$m.

The solid catalysts of the present invention, optionally prepolymerized, may be used in an addition polymerization process wherein one or more addition polymerizable monomers are contacted with the solid catalyst of the invention under addition polymerization conditions.

Suitable addition polymerizable monomers include ethylenically unsaturated monomers, acetylenic compounds, conjugated or nonconjugated dienes, polyenes, and carbon monoxide. Preferred monomers include olefins, for examples alpha-olefins having from 2 to about 20, preferably from about 2 to about 12, more preferably from about 2 to about 8 carbon atoms and combinations of two or more of such alpha-olefins. Particularly suitable alpha-olefins include, for example, ethylene, propylene, 1-butene, 1-pentene, 4-methylpentene-1, 1-hexene, 1-heptene, 1-octene, 1-nonene, 1-decene, 1-undecene, 1-dodecene, 1-tridecene, 1-tetradecene, 1-pentadecene, or combinations thereof. Preferably, the alpha-olefins are ethylene, propylene, 1-butene, 4-methyl-pentene-1, 1-pentene, 1-hexene, 1-octene, and combinations of ethylene and/or propylene with one or more of such other alpha-olefins. Most preferably, ethylene or propylene is used as one of the addition polymerizable monomers. Suitable dienes include those having from 4 to 30 carbon atoms, especially those having 5 to 18 carbon atoms. Typical of these are α,ω-dienes, α-internal dienes, including those dienes which are typically used for preparing EPDM type elastomers. Typical examples include 1,3-butadiene, 1,3- and 1,4-pentadiene, 1,3-, 1,4-, and 1,5-hexadiene, 1,7-octadiene, 1,9-decadiene, and lower alkyl substituted analogues of any of these. Other preferred monomers include styrene, halo- or alkyl substituted styrenes, tetrafluoroethylene, vinylcyclobutene, dicyclopentadiene, and ethylidene norbornenes. Suitable addition polymerizable monomers include also any mixtures of the above-mentioned monomers.

The solid catalyst can be formed in situ in the polymerization mixture by introducing into the mixture the catalyst components (a), (b), (c), and optionally (d).

The solid catalysts of this invention, both supported and nonsupported, as well as the homogeneous catalysts, may he used in various catalysts systems, either alone or with other catalyst components or other catalysts, where the catalyst of this invention is an integral part of the catalyst system.

The catalyst may be used in the polymerization reaction in a concentration of $10^{-9}$ to $10^{-3}$ moles, based on transition metal, per liter diluent or reaction volume, but is preferably used in a concentration of less than $10^{-5}$, preferably from $10^{-8}$ to $9 \times 10^{-6}$ moles per liter diluent or reaction volume.

The solid catalysts can be advantageously employed in a high pressure, solution, slurry, or gas phase polymerization process. For a solution polymerization process it is desirable to redissolve the solid catalyst or to employ homogeneous solutions of the catalyst components. A high pressure process is usually carried out at temperatures from 100° C. to 400° C. and at pressures above 500 bar. A slurry process typically uses an inert hydrocarbon diluent and temperatures of from about 0° C. up to a temperature just below the temperature at which the resulting polymer becomes substantially soluble in the inert polymerization medium. Preferred temperatures are from about 30° C., preferably from about 60° C. to about 115° C., preferably to about 100° C. The solution process is carried out at temperatures from the temperature at which the resulting polymer is soluble in an inert solvent up to about 275° C. Generally, solubility of the polymer depends on its density. For ethylene copolymers having densities of 0.86 g/cm³, solution polymerization may be achieved at temperatures as low as about 60° C. Preferably, solution polymerization temperatures range from about 75° C., more preferably from about 80° C., and typically from about 130° C. to about 260° C., more preferably to about 170° C. Most preferably, temperatures in a solution process are between about 80° C. and 150° C. As inert solvents typically hydrocarbons and preferably aliphatic hydrocarbons are used. The solution and slurry processes are usually carried out at pressures between about 1 to 100 bar. Typical operating conditions for gas phase polymerizations are from 20° C. to 100° C., more preferably from 40° C. to 80° C. In gas phase processes the pressure is typically from subatmospheric to 100 bar.

Preferably for use in gas phase polymerization processes, the solid catalyst has a median particle diameter from about 20 to about 200 μm, more preferably from about 30 μm to about 150 μm, and most preferably from about 50 μm to about 100 μm. Preferably for use in slurry polymerization processes, the support has a median particle diameter from about 1 μm to about 200 μm, more preferably from about 5 μm to about 100 μm, and most preferably from about 10 μm to about 80 μm. Preferably for use in solution or high pressure polymerization processes, the support has a median particle diameter from about 1 μm to about 40 μm, more preferably from about 2 μm to about 30 μm, and most preferably from about 3 μm to about 20 μm.

In the polymerization processes of the present invention impurity scavengers may be used which serve to protect the solid catalyst from catalyst poisons such as water, oxygen, and polar compounds. These scavengers can generally be used in amounts depending on the amounts of impurities. Typical scavengers include organometal compounds, and preferably trialkylaluminum or boron compounds and alumoxanes. Further, antistatic agents may be introduced into the reactor to prevent agglomeration or sticking of polymer or catalyst to the reactor walls.

In the present polymerization processes also molecular weight control agents can be used, such as hydrogen or other chain transfer agents. The polymers that are prepared according to such polymerization process may be combined with any conventional additives, such as UV stabilizers, antioxidants, anti-slip or anti-blocking agents, which may be added in conventional ways, for example, downstream of the polymerization reactor, or in an extrusion or molding step.

Upon or after removal of the polymerization mixture or product of from the polymerization reactor, the supported catalyst may be deactivated by exposure to air or water, or through ally other catalyst deactivating agent or procedure.

Suitable solvents for the various polymerization processes are inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and the like and aromatic and alkyl-substituted aromatic compounds such as benzene, toluene, xylene, ethylbenzene and the like. Suitable solvents also include liquid olefins which may act as monomers or comonomers including ethylene, propylene, butadiene, 1-butene, cyclopentene, 1-hexene, 1-heptene, 4-vinylcyclohexene, vinylcyclohexane, 3-methyl-1-pentene, 4-methyl-1-pentene, 1,4-hexadiene, 1-octene, 1-decene, styrenes divinylbenzene, allylbenzene, vinyltoluene (including all isomers alone or in admixture), and the like. Mixtures of the foregoing are also suitable.

The catalyst systems may be utilized in combination with at least one additional homogeneous or heterogeneous polymerization catalyst in separate reactors connected in series or in parallel to prepare polymer blends having desirable properties. An example of such a process is disclosed in WO-94/00500, equivalent to U.S. Ser. No. 07/904.770, as well as U.S. Ser. No. 08/10958, filed Jan. 29, 1993, the teachings of which are hereby incorporated by reference herein.

Utilizing, the catalyst systems of the present invention, particularly for solution polymerization, copolymers having high comonomer incorporation and correspondingly low density, yet having a low melt index may be readily prepared. That is, high molecular weight polymers are readily attained by use of the present catalysts even at elevated reactor temperatures. This result is highly desirable because the molecular weight of α-olefin copolymers can be readily reduced by the use of hydrogen or similar chain transfer agent, however increasing the molecular weight of α-olefin copolymers is usually only attainable by reducing the polymerization temperature of the reactor. Disadvantageously, operation of a polymerization reactor at reduced temperatures significantly increases the cost of operation since heat must be removed from the reactor to maintain the reduced reaction temperature, while at the same time heat must be added to the reactor effluent to vaporize the solvent. In addition, productivity is increased due to improved polymer solubility, decreased solution viscosity, and a higher polymer concentration. Utilizing the present catalysts, α-olefin in homopolymers and copolymers having densities from 0.85 g/cm³ to 0.96 g/cm³, and melt flow rates from 0.001 to 10.0 dg/min are readily attained in a high temperature process.

The solid catalysts of the present invention, also when used in a slurry process or gas phase process, not only are able to produce ethylene copolymers of densities typical for high density polyethylene, in the range of 0.980 to 0.940 g/cm$^3$, but surprisingly, also enable the production of copolymers having substantially lower densities. Copolymers of densities lower than 0.940 g/cm$^3$ and especially lower than 0.930 g/cm$^3$ down to 0.880 g/cm$^3$ or lower can be made while providing free flowing polymers, retaining good bulk density properties and while preventing or substantially eliminating reactor fouling. The present invention is capable of producing olefin polymers and copolymers having weight average molecular weights of more than 30,000, preferably more than 50,000, most preferably more than 100,000 up to 1,000,000 and even higher. Typical molecular weight distributions $M_w/M_n$ range from 1.5 to 15, or even higher, preferably between 2.0 and 8.0.

The catalyst systems of the present invention are particularly advantageous for the production of ethylene homopolymers and ethylene/α-olefin copolymers having high levels of long chain branching, especially in solution polymerizations and in gas phase polymerization processes. The use of the catalyst systems of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalysts system advantageously allows for the economical production of ethylene/α-olefin copolymers having processability similar to high pressure, free radical produced low density polyethylene.

In another aspect of the processes of this invention, a preferred process is a high temperature solution polymerization process for the polymerization of olefins comprising contacting one or more $C_{2-20}$ α-olefins under polymerization conditions 25 with a catalyst system of this invention at a temperature from about 100° C. to about 250° C. More preferred as a temperature range for this process is a temperature from about 120° C. to about 200° C., and even more preferred is temperature from about 150° C. to about 200° C.

The present catalysts system may be advantageously employed to prepare olefin polymers having improved processing properties by polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise a $C_{3-20}$ α-olefin, including ethylene, and a "H"-branching comonomer. Preferably, such polymers are produced in a solution process, most preferably a continuous solution process. Alternatively, such polymers may be produced in a gas phase process or a slurry process, as disclosed in U.S. application Ser. No. 08/857817 filed May 16, 1997; U.S. application Ser. No. 08/857816 filed May 16, 1997; and PCT Application No. PCT/US97/08466 filed May 16, 1997, all of which are hereby incorporated by reference.

As previously mentioned, the present catalyst system is particularly useful in the preparation of EP and EPDM copolymers in high yield and productivity. The process employed may be either a solution or slurry process both of which are previously known in the art. Kaminsky, *J. Poly. Sci.*, Vol. 23, pp. 2151–64 (1985) reported the use of a soluble bis(cyclopentadienyl) zirconium dimethyl-alumoxane catalyst system for solution polymerization of EP and EPDM elastomers. U.S. Pat. No. 5,229,478 disclosed a slurry polymerization process utilizing similar bis (cyclopentadienyl) zirconium based catalyst systems.

In general terms, it is desirable to produce such EP and EPDM elastomers under conditions of increased reactivity of the diene monomer component. The reason for this was explained in the above-identified '478 patent in the following manner, which still remains true despite the advances attained in such reference. A major factor affecting production costs and hence the utility of an EPDM is the diene monomer cost. The diene is a more expensive monomer material than ethylene or propylene. Further, the reactivity of diene monomers with previously known metallocene catalysts is lower than that of ethylene and propylene. Consequently, to achieve the requisite degree of diene incorporation to produce an EPDM with an acceptably fast cure rate, it has been necessary to use a diene monomer concentration which, expressed as a percentage of the total concentration of monomers present, is in substantial excess compared to the percentage of diene desired to be incorporated into the final EPDM product. Since substantial amounts of unreacted diene monomer must be recovered from the polymerization reactor effluent for recycle, the cost of production is increased unnecessarily.

Further adding to the cost of producing an EPDM is the fact that, generally, the exposure of an olelin polymerization catalyst to a diene, especially the high concentrations of diene monomer required to produce the requisite level of diene incorporation in the final EPDM product, often reduces the rate or activity at which the catalyst will cause polymerization of ethylene and propylene monomers to proceed. Correspondingly, lower throughputs and longer reaction times have been required. compared to the production of an ethylene-propylene copolymer elastomer or other α-olefin copolymer elastomer.

The present catalyst system advantageously allows for increased diene reactivity thereby preparing EPDM polymers in high yield and productivity. Additionally, the catalyst system of the present invention achieves the economical production of EPDM polymers with diene contents of up to 20 weight percent or higher, which polymers possess highly desirable fast cure rates.

The nonconjugated diene monomer can be a straight chain, branched chain or cyclic hydrocarbon diene having from about 6 to about 15 carbon atoms. Examples of suitable nonconjugated dienes are straight chain acyclic dienes such as 1,4-hexadiene and 1,6-octadiene: branched chain acyclic dienes such as 5-methyl-1,4-hexadiene; 3,7-dimethyl-1,6-octadiene: 3,7-dimethyl-1,7-octadiene and mixed isomers of dihydromyricene and dihydroocinene; single ring alicyclic dienes such as 1,3-cyclopentadiene; 1,4-cyclohexadiene; 1,5-cyclooctadiene and 1,5-cyclododecadiene: and multiring alicyclic fused and bridged ring dienes such as tetrahydroindene, methyl tetrahydroindene, dicyclopentadiene; bicyclo-(2,2,1)-hepta-2,5-diene; alkenyl, alkylidene, cycloalkenyl and cycloalkylidene norbornenes such as 5-methylene-2-norbornene (MNB); 5-propenyl-2-norbornene, 5-isopropylidene-2-norbornene. 5-(4-cyclopentenyl)-2-norbornene, 5-cyclohexylidene-2-norbornene, 5-vinyl-2-norbornene and norbornadiene.

Of the dienes typically used to prepare EPDMs, the particularly preferred dienes are 1,4-hexadiene (HD), 5-ethylidene-2-norbornene (ENB), 5-vinylidene-2-norbornene (VNB), 5-methylene-2-norbornene (MNB), and dicyclopentadiene (DCPD). The especially preferred dienes are 5-ethylidene-2-norbornene (ENB) and 1,4-hexadiene (HD).

The preferred EPDM elastomers may contain about 20 up to about 90 weight percent ethylene, more preferably about 30 to 85 weight percent ethylene, most preferably about 35 to about 80 weight percent ethylene.

The alpha-olefins suitable for use in the preparation of elastomers with ethylene and dienes are preferably $C_{3-16}$ alpha-olefins. Illustrative nonlimiting examples of such alpha-olefins are propylene, 1-butene, 1-pentene, 1-hexene, 4-methyl-1-pentene, 1-heptene, 1-octene, 1-decene, and 1-dodecene. The alpha-olefin is generally incorporated into the EPDM polymer at about 10 to about 80 weight percent, more preferably at about 20 to about 65 weight percent. The nonconjugated dienes are generally incorporated into the EPDM at about 0.5 to about 20 weight percent; more, preferably at about 1 to about 15 weight percent, and most preferably at 3 to about 12 weight percent. If desired, more than one diene may be incorporated simultaneously, for example HD and ENB, with total diene incorporation within the limits specified above.

At all times, the individual ingredients as well as the recovered catalyst components must be protected from oxygen and moisture. Therefore, the catalyst components and catalysts must be prepared and recovered in an oxygen and moisture-free atmosphere. Preferably, therefore, the reactions are performed in the presence of a dry, inert gas such as, for example. nitrogen.

The polymerization may be carried out as a batchwise or a continuous polymerization process. A continuous process is preferred, in which event catalyst components, ethylene, α-olefin, and optionally solvent and diene are continuously supplied to the reaction zone and polymer product continuously removed therefrom. Within the scope of the terms "continuous" and "continuously" as used in this context are those processes in which there are intermittent additions of reactants and removal of products at small regular intervals, so that, over time the overall process is continuous.

In a preferred manner of operation, the polymerization is conducted in a continuous solution polymerization system comprising two reactors connected in series or parallel. In one reactor a relatively high molecular weight product (Mw from 300,000 to 600,000, more preferably 400,000 to 500,000) is formed while in the second reactor a product of a relatively low molecular weight (Mw 50,000 to 300,000) is formed. The final product is a blend of the two reactor effluents which are combined prior to devolatilization to result in a uniform blend of the two polymer products. Such a dual reactor process allows for the preparation of products having, improved properties. In a preferred embodiment the reactors are connected in series, that is effluent from the first reactor is charged to the second reactor and fresh monomer, solvent and hydrogen is added to the second reactor. Reactor conditions are adjusted such that the weight ratio of polymer produced in the first reactor to that produced in the second reactor is from 20:80 to 80:20. In addition the temperature of the second reactor is controlled to produce the lower molecular weight product. This system beneficially allow for production of EPDM products having a large range of Mooney viscosities, as well as excellent strength and processability. Preferably the Mooney viscosity (ASTM D1646-94, ML1+4@125° C.) of the resulting product is adjusted to fail in the range from 1 to 200, preferably from 5 to 150 and most preferably from 10 to 110.

The polymerization process of the present invention can he employed to advantage in the gas phase copolymerization of olefins. Gas phase processes for the polymerization of olefins, especially the homopolymerization and copolymerization of ethylene and propylene, and the copolymerization of ethylene with higher α-olefins such as, for example, 1-butene, 1-hexene, 4-methyl-1-pentene are well known in the art. Such processes are used commercially on a large scale for the manufacture of high density polyethylene (HIDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported or suspended above a perforated plate, the fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means or a blower or compressor and one or more heat exchangers to strip the gas of the heat of polymerization.

A preferred method of cooling of the bed, in addition to the cooling provided by the cooled recycle gas, is to feed a volatile liquid to the bed to provide an evaporative cooling effect, often referred to as operation in the condensing mode. The volatile liquid employed in this case can be, for example, a volatile inert liquid, for example, a saturated hydrocarbon having about 3 to about 8, preferably 4 to 6, carbon atoms. In the case that the monomer or comonomer itself is a volatile liquid, or can be condensed to provide such a liquid this can suitably be fed to the bed to provide an evaporative cooling effect. Examples of olefin monomers which can be employed in this manner are olefins containing about three to about eight, preferably three to six carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle as, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream. This type of process is described, for example in EP-8969 1; U.S. Pat. No. 4,543,399; WO-94/25495 and U.S. Pat. No. 5,352,749, which are hereby incorporated by reference. A particularly preferred method of recycling the liquid to the bed is to separate the liquid from the recycle gas stream and to reinject this liquid directly into the bed, preferably using a method which generates fine droplets of the liquid within the bed. This type of process is described in BP Chemicals' WO-94/28032, which is hereby incorporated by reference.

The polymerization reaction occurring in the gas fluidized bed is catalyzed by the continuous or semi-continuous addition of catalyst. Such catalyst can be supported on an inorganic or organic support material as described above. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed copolymerization of the monomer and one or more comonomers on the fluidized particles of catalyst, supported catalyst or prepolymer within the bed. Start-up of the polymerization reaction is achieved using a bed of preformed polymer particles, which are preferably similar to the target polyolefin, and conditioning the bed by drying with inert gas or nitrogen prior to introducing the catalyst, the monomers and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired.

The gas phase processes suitable for the practice of this invention are preferably continuous processes which provide for the continuous supply of reactants to the reaction zone of the reactor and the removal of products from the reaction zone of the reactor, thereby providing a steady-state environment on the macro scale in the reaction zone of the reactor.

Typically, the fluidized bed of the gas phase process is operated at temperatures greater than 50° C., preferably from about 60° C. to about 110° C., more preferably from about 70° C. to about 110° C.

Typically the molar ratio of comonomer to monomers used in the polymerization depends upon the desired density for the composition being produced and is about 0.5 or less. Desirably, when producing materials with a density range of from about 0.91 to about 0.93 the comonomer to monomer ratio is less than 0.2, preferably less than 0.05, even more preferably less than 0.02, and may even be less than 0.01. Typically, the ratio of hydrogen to monomer is less than about 0.5, preferably less than 0.2, mote preferably less than 0.05, even more preferably less than 0.02 and may even he less than 0.01.

The above-described ranges of process variables are appropriate for the gas phase process of this invention and may be suitable for other processes adaptable to the practice of this invention.

A number of patents and patent applications describe gas phase processes which are adaptable for use in the process of this invention, particularly, U.S. Pat. Nos. 4,588,790; 4,543,399; 5,352,749; 5,436,304; 5,405,922; 5,462,999; 5,461,123; 5,453,471; 5,032,562; 5,028,670; 5,473,028; 5,106,804; 5,556,238; 5,541,270; 5,608,019; 5,616,661; and EP applications 659,773; 692,500; 780,404; 697,420; 628,343; 593,083; 676,421; 683,176; 699,212; 699,213; 721,798; 728;150: 728,151; 728,771; 728,772; 735,058; and PCT Applications WO-94/29032, WO-94/25497, WO-94/25495, WO-94/28032, WO-95/13305, WO-94/26793, WO-95/07942, WO-97/25355, WO-93/11171, WO-95/13305, and WO-95/13306, all of which are hereby incorporated herein by reference.

For the preferred polyolefin polymer compositions of this invention, which may be produced by the polymerization processes of this invention using the catalyst systems of this invention, the long chain branch is longer than the short chain branch that results from the incorporation of one or more α-olefin comonomers into the polymer backbone. The empirical effect of the presence of long chain branching in the copolymers of this invention is manifested as enhanced rheological properties which are indicated by higher flow activation energies, and greater $I_{21}/I_2$ than expected from the other structural properties of the compositions.

Further, highly preferred polyolefin copolymer compositions of this invention have reverse molecular architecture, that is, there is a molecular weight maximum which occurs in that 50 percent by weight of the composition which has the highest weight percent comonomer content. Even more preferred are polyolefin copolymer compositions which also halve long chain branches along the polymer backbone, especially when produced with a catalyst system of this invention having a single metallocene complex of this invention in a single reactor in a process for the polymerization of all α-olefin monomer with one or more olefin comonomers, more especially when the process is a continuous process.

Measurement of Comonomer Content vs. Log Molecular Weight by GPC/FTIR

The comonomer content as a function of molecular weight was measured by coupling a Fourier transform infrared spectrometer (FTIR) to a Waters 150° C. Gel Permeation Chromatograph (GPC). The setting up, calibration and operation of this system together with the method for data treatment has been described previously (L. J. Rose et al, "Characterisation of Polyethylene Copolymers by Coupled GPC/FTIR" in "Characterisation of Copolymers", Rapra Technology, Shawbury UK, 1995, ISBN 1-85957-048-86.) In order to characterize the degree to which the comonomer is concentrated in the high molecular weight part of the polymer, the GPC/FTIR was used to calculate a parameter named comonomer partition factor, $C_{pf}$. $M_n$ and $M_w$ were also determined using standard techniques from the GPC data.

Comonomer Partitioning Factor (GPC-FTIR)

The comonomer partitioning factor $C_{pf}$ is calculated from GPC/FTIR data. It characterizes the ratio of the average comonomer content of the higher molecular weight fractions to the average comonomer content of the lower molecular weight fractions. Higher and lower molecular weight are defined as being above or below the median molecular weight respectively, that is, the molecular weight distribution is divided into two parts of equal weight. $C_{pf}$ is calculated from the following equation:

$$C_{pf} = \frac{\frac{\sum_{i=1}^{n} w_i \cdot c_i}{\sum_{i=1}^{n} w_i}}{\frac{\sum_{j=1}^{m} w_j \cdot c_j}{\sum_{j=1}^{m} w_j}},$$

where: $c_i$ is the mole fraction comonomer content and $w_i$ is the normalized weight fraction as determined by GPC/FTIR for the n FTIR data points above the median molecular weight, $c_j$ is the mole fraction comonomer content and $w_j$ is the normalized weight fraction as determined by GPC/FTIR for the m FTIR data points below the median molecular weight. Only those weight fractions, $w_i$ or $w_j$ which have associated mole fraction comonomer, content values are used to calculate $C_{pf}$. For a valid calculation it is required that n and m are greater than or equal to 3. FTIR data corresponding to molecular weight fractions below 5,000 are not included in the calculation due to the uncertainties present in such data.

For the polyolefin copolymer compositions of this invention, $C_{pf}$ desirably is equal to or greater than 1.10, more desirably is equal to or greater than 1.15, even more desirably is equal to or greater than 1.20, preferably is equal to or greater than 1.30, more preferably is equal to or greater than 1.40, even more preferably is equal to or greater than 1.50, and still more preferably is equal to or greater than 1.60.

ATREF-DV

ATREF-DV has been described in U.S. Pat. No. 4,79,081, which is hereby incorporated by reference, and in "Determination of Short-Chain Branching Distributions of Ethylene copolymers by Automated Analytical Temperature Rising Elution Fractionation" (Auto-ATREF), *J. of Appl Pol Sci*: Applied Polymer Symposium 45, 25–37 (1990). ATREF-DV is a dual detector analytical system that is capable of fractionating semi-crystalline polymers like Linear Low Density Polyethylene (LLDPE) as a function of crystallization temperature while simultaneously estimating the molecular weight of the fractions. With regard to the fractionation, ATREF-DV is analogous to Temperature Rising Elution Fractionation (TREF) analysis that have been published in the open literature over the past 15 years. The primary difference is that this Analytical—TREF (ATREF) technique is done on a small scale and fractions are not actually isolated. Instead, a typical liquid chromatographic (LC) mass detector, such as an infrared single frequency detector is used to quantify the crystallinity distribution as a function of elution temperature. This distribution can then be transformed to any number of alternative domains such as short branching frequency, comonomer distribution, or possibly density. Thus, this transformed distribution can then be interpreted according to some structural variable like comonomer content, although routine use of ATREF for comparisons of various LLDPE's is often done directly in the elution temperature domain.

To obtain ATREF-DV data, a commercially available viscometer especially adapted for LC analysis, such as a Viskotek™ is coupled with the IR mass detector. Together these two LC detectors can be used to calculate the intrinsic viscosity of the ATREF-DV eluant. The viscosity average molecular weight of a given fraction can then be estimated using appropriate Mark Hoodwink constants, the corresponding intrinsic viscosity, and suitable coefficients to estimate the fractions concentration (dl/g) as it passes through the detectors. Thus, a typical ATREF-DV report will provide the weight fraction polymer and viscosity average molecular weight as a function of elution temperature. $M_{pf}$ is then calculated using the equation given.

Molecular Weight Partitioning Factor

The molecular weight partitioning factor $M_{pf}$ is calculated from TREF/DV data. It characterizes the ratio of the average molecular weight of the fractions with high comonomer content to the average molecular weight of the fractions with low comonomer content. Higher and lower comonomer content are defined as being below or above the median elution temperature of the TREF concentration plot respectively, that is, the TREF data is divided into two parts of equal weight. $M_{pf}$ is calculated from the following equation:

$$M_{pf} = \frac{\frac{\sum_{i=1}^{n} w_i \cdot M_i}{\sum_{i=1}^{n} w_i}}{\frac{\sum_{j=1}^{m} w_j \cdot M_j}{\sum_{j=1}^{m} w_j}},$$

where: $M_i$ is the viscosity average molecular weight and $w_i$ is the normalized weight fraction as determined by ATREF-DV for the n data points in the fractions below the median elution temperature. $M_j$ is the viscosity average molecular weight and $w_j$ is the normalized weight fraction as determined by ATREF-DV for the m data points in the fractions above the median elution temperature. Only those weight fractions, $w_i$ or $w_j$ which have associated viscosity average molecular weights greater than zero are used to calculate $M_{pf}$. For a valid calculation, it is required that n and m ale greater than or equal to 3.

For the polyolefin copolymer compositions of this invention, $M_{pf}$ desirably is equal to or greater than 1.15, more desirably is equal to or greater than 1.30, even more desirably is equal to or greater than 1.40, preferably is equal to or greater than 1.50, more preferably is equal to or greater than 1.60, even more preferably is equal to or greater than 1.70.

Having described the invention the following examples are provided as further illustration thereof and are not to be construed as limiting. Unless stated to the contrary all parts and percentages are expressed on a weight basis.

EXAMPLES

The bulk density of the polymers produced in the present examples was determined according to ASTM 1895. All experiments were carried out under the exclusion of oxygen and water under a nitrogen atmosphere, unless indicated otherwise.

Preparation of the Hydrochloride of Kemnamine™ T9701

Kemamine™ T9701, (NMe($C_{18-22}H_{37-45}$)$_2$(13.4 gram, 25 mmol), available from Witco Corp. (Kemamine is a trademark of Witco Corp.) was dissolved in diethylether (300 ml). Hydrogen chloride gas was bubbled through the solution for 5 minutes, until the pH was acidic as shown by pH paper. The mixture was stirred for 15 minutes and the white precipitate was collected by filtration, washed with three 50 ml portions of diethylether and dried under vacuum. The yield of the NHClMe($C_{18-22}H_{37-45}$)$_2$ was 12.6 gram.

Preparation of [(p-HOC$_6$H$_4$)B(C$_6$F$_5$)$_3$][NHMe(C$_{18-22}$H$_{37-45}$)$_2$]

NHClMe($C_{18-22}H_{37-45}$)$_2$ (4.58 gram, 8 mmol) was dissolved in dichloromethane (50 ml). Trimethylammonium tris(pentafluorophenyl)(4-hydroxyphenyl)borate [(p-HOC$_6$H$_4$)B(C$_6$F$_5$)$_3$][NHEt$_3$] (5.66 gram, 8 mmol, prepared as substantially described in Example 1B of U.S. patent application Ser. No. 08/610,647, filed Mar. 4, 1996 (corresponding to WO-96/28480)) was added followed by 40 ml distilled water. The mixture was rapidly agitated for 4 hours and then the water layer was removed by syringe. The dichloromethane layer was washed three times with 40 ml portions of distilled water. The dichloromethane layer was then dried over sodium sulphate, filtered and vacuum dried to yield an oil. The oil was extracted into toluene (200 ml), the resulting solution was filtered and the filtrate was vacuum dried to yield 8.84 gram of a colorless oil.

Example 1

Preparation of Catalyst 1 ml of a 0.031M solution of [(p-HOC$_6$H$_4$)B(C$_6$F$_5$)$_3$] [NHMe(C$_{18-22}$H$_{37-45}$)$_2$] in toluene was treated with 18 ml of n-hexane by adding the n-hexane yielding a cloudy suspension which was stirred for 5 minutes. A solution of titanium, (N-1,1-dimethylethyl)dimethyl(1-(1,2,3,4,5-eta)-2,3,4,5-tetramethyl-2,4-cyclopentadien-1-yl)silanaminato))(2-)N)-($\eta^4$-1,3-pentadiene) (C$_5$Me$_4$SiMe$_2$N$^t$Bu)Ti($\eta^4$-1,3-pentadiene) (0.33 ml of a 0.0925 M solution in Isopar™ E; Isopar™ E, a trademark of Exxon Chemical Company, is a mixture of C$_8$ saturated hydrocarbons) was added to generate a red-brown colored suspension. After 5 minutes while stirring a 6 ml aliquot of this mixture was treated with 0.2 mmol of triethylaluminum (2 ml of a 0.1 M solution in n-hexane) and the mixture was stirred for a further 15 minutes before using as such in a polymerization reaction.

Slurry Phase Polymerization

A stirred 5 liter reactor was charged with 100 μmol of triisobutylaluminum, 3 liters of hexane and 0.5 normal liter of hydrogen before heating to 60° C. Ethylene was then added to the reactor in an amount sufficient to bring the total pressure to 10 bar. An aliquot of the catalyst prepared as described above containing 10 μmol of titanium was then added to initiate the polymerization. The reactor pressure was kept essentially constant by continually feeding ethylene on demand during the polymerization reaction. The temperature was kept substantially constant by cooling the reactor as required. After 49 minutes the ethylene feed was shut off and the contents of the reactor were transferred to a sample pan. After drying, 925 g of a free flowing polyethylene powder was obtained. The efficiency was calculated to be 1,931,100 g polyethylene PE/g Ti and the bulk density 0.29 g/cm$^3$. Scanning electron micrographs of the polymer powder indicated the presence of spherical particles having a smooth surface morphology.

Example 2 (Comparative)

The slurry polymerization procedure of Example 1 was repeated, yet without using triethylaluminum in the catalyst preparation step, without adding triisobutylaluminium to the reactor, and while using an amount of 30 μmol of titanium for the polymerization reaction. No polyethylene product was obtained.

Example 3

1 ml of a 0.031 M solution of [(p-HOC$_6$H$_4$)B(C$_6$F$_5$)$_3$] [NHMe(C$_{18-22}$H$_{37-45}$)$_2$] in toluene was treated with 10 ml of n-hexane yielding a cloudy suspension and the mixture was stirred for 5 minutes. A mixture of a solution of (C$_5$Me$_4$SiMe$_2$N$^t$Bu)Ti($\eta^4$-1,3-pentadiene) (0.33 ml of a 0.0925 M solution in Isopar™ E) and 0.3 mmol of triethylaluminum (3 ml of a 0.1 M solution in n-hexane) was added and the mixture was stirred for 15 minutes. An aliquot of this mixture containing 10 micromol of titanium was used as such in a polymerization reaction.

The polymerization conditions were identical to those of Example 1 except that the duration was 48 minutes. After drying, 850 gram of a free flowing polyethylene powder was obtained. The efficiency was calculated to be 1,774,530 g PE/g Ti.

Example 4

0.5 ml of a 0.031 M solution of [(p-HOC$_6$H$_4$)B(C$_6$F$_5$)$_3$] [NHMe(C$_{18-22}$H$_{37-45}$)$_2$] in toluene was treated with 5 ml of n-hexane yielding a cloudy suspension and the mixture was stirred for 5 minutes. 0.075 mmol of triethylaluminum (0.75 ml of a 0.1 M solution in n-hexane) was added and the mixture was stirred for 5 minutes. A solution of (C$_5$Me$_4$SiMe$_2$N$^t$Bu)Ti($\eta^4$-1,3-pentadiene) (0.16 ml of a 0.0925 M solution in Isopar™ E) was added and the mixture stirred for 5 minutes. This mixture was used as such in a polymerization reaction.

The polymerization conditions were identical to those of Example 1 except that the duration was 30 minutes. After drying, 630 gram of a free flowing polyethylene powder was obtained. The efficiency was calculated to be 888,675 g PE/g Ti.

Example 5

40 gram of silica SP12 (Grace Davison) which had been heated at 250° C. for 3 hours under vacuum was slurried in toluene (400 ml) and then treated with 40 ml of triethylaluminum in 250 ml toluene. The mixture was stirred for 1 hour, filtered and the treated silica was washed with toluene (100 ml, of about 100° C.) and dried under high vacuum.

10 ml of a 0.031 M solution of [(p-HOC$_6$H$_4$)B(C$_6$F$_5$)$_3$] [NHMe(C$_{18-22}$H$_{37-45}$)$_2$] in toluene was treated with 40 ml of n-hexane yielding a cloudy suspension. The mixture was stirred for 5 minutes. 3.1 mmol of triethylaluminum (15.5 ml of a 0.2 M solution in n-hexane) was added and the mixture was stirred for 5 minutes. An aliquot of this suspension containing 40 μmole of the borate was treated with 40 μmole of a solution of (C$_5$Me$_4$SiMe$_2$ N$^t$Bu)Ti($\eta^4$-1,3-pentadiene) (0.43 ml of a 0.0925 M solution in Isopar™ E). The resulting suspension was added to a slurry of 1 gram of the silica treated as described above, in 20 ml of hexane. The mixture was stirred for 5 minutes and then an aliquot of the mixture containing 15 μmole of titanium was used as such in a slurry polymerization.

The polymerization conditions were identical to those of Example 1 except that the polymerization time was 30 minutes. 600 grams of a free flowing polyethylene powder was isolated of bulk density 0.31 g/cm$^3$. The efficiency was calculated to be 835,070 g PE/g Ti.

Example 6

2 gram of triethylaluminum treated silica (prepared as in Example 5) were placed in a 20 ml flask. In a separate vessel 1.23 ml of a solution of [(p-HO—C$_6$H$_4$)B(C$_6$F$_5$)$_3$][NHMe (C$_{18-22}$H$_{37-45}$)$_2$] (0.065 M) in toluene containing 80 micromol of the borate was diluted with a further 1 ml of toluene. 0.13 ml of a 0.6 M solution of triethylaluminum in hexane was added and the mixture stirred for 10 minutes.

The borate/TEA solution, the volume of which about corresponded to the pore volume of the support material, was added to the treated support material and the mixture agitated. 8 ml of hexane was added to the dry powder to give a slurry followed by a solution of (C$_5$Me$_5$SiMe$_2$N$^t$Bu)Ti($\eta^4$-1,3-pentadiene) (0.86 ml of a 0.0925M solution in Isopar™ E) to yield a green colored supported catalyst.

The polymerization conditions were identical to those of Example 1 except that the polymerization time was 36 minutes and an aliquot of catalyst containing 15 micromol Ti was used. 260 gram of free flowing polymer powder of bulk density 0.25 g/cm$^3$ was obtained. The efficiency was 361, 860 g PE/g Ti.

Example 7

1 ml of a 0.031M solution of [(p-HOC$_6$H$_4$)B(C$_6$F$_5$)$_3$] [NHMe(C$_{18-22}$H$_{37-45}$)$_2$] in toluene was treated with 10 ml of n-hexane to yield a cloudy suspension. In a separate vessel 0.33 ml of a 0.08M solution of (n-BuCp)$_2$ZrCl$_2$ in toluene was treated with 3 ml of a 0.1M solution of triethylaluminum in n-hexane followed by 2 ml of n-hexane. The zirconocene solution was added to the borate suspension and the mixture agitated for a few minutes. An aliquot of the catalyst prepared as above containing 10 μmol of zirconium was used in a polymerization reaction. 580 g of a free flowing polyethylene powder was obtained after 55 minutes. The efficiency was calculated to be 317,912 g PE/g Zr.

Example 8

0.43 ml of a 0.092M solution of [(p-HOC$_6$H$_4$)B(C$_6$F$_5$)$_3$][NHMe(C$_{18-22}$H$_{37-45}$)$_2$] in toluene was treated with 0.40 ml of a 0.1M solution of triethylaluminum in toluene. 10 ml of n-hexane was added to yield a fine precipitate. 0.31 ml of a 0.13M solution of (C$_5$Me$_4$SiMe$_2$N$^t$Bu)Ti(η$^4$-1,3-pentadiene) in Isopar™ E was added and the mixture agitated for a few minutes. An aliquot of the catalyst containing 20 μmol of titanium was used in a polymerization reaction. No alkylaluminum scavenger was used and 0.3 liter of hydrogen was added. 420 g of a free flowing polyethylene powder was obtained after 30 minutes. The bulk density was 0.22 g/cm3 and the efficiency was calculated to be 438,413 PE/g Ti.

Example 9

0.43 ml of a 0.092M solution of [(p-HOC$_6$H$_4$)B(C$_6$F$_5$)$_3$][NHMe(C$_{18-22}$H$_{37-45}$)$_2$] in toluene was treated with 10 ml of n-hexane to give a cloudy suspension. 0.31 ml of a 0.13M solution of (C$_5$Me$_4$SiMe$_2$N$^t$Bu)Ti(η$^4$-1,3-pentadiene) in Isopar™ E was added to yield an orange-brown colored suspension. An aliquot of this suspension containing 20 μmol Ti was used in a polymerization reaction. 500 μmol of triethylaluminum was added as a preload to the reactor. 120 g of a free flowing polyethylene powder was obtained after 15 minutes. The efficiency was calculated to be 125,260 g PE/g Ti.

Example 10

1 gram of triethylaluminum treated silica (prepared as in Example 5 but using a 45 micron silica gel, Grace Davison) were placed in a 20 ml flask. In a separate vessel, 0.43 ml of a solution of [(p-HOC$_6$H$_4$)B(C$_6$F$_5$)$_3$][NHMe(C$_{18-22}$H$_{37-45}$)$_2$] in toluene was treated with 0.40 ml of a 0.1M solution of triethylaluminum. The resulting solution was added to the treated support material and the mixture agitated. 10 ml of n-hexane was added to slurry the support followed by a solution of 0.031 g of rac-Me$_2$Si(2-methyl-4-phenyl-indenyl)$_2$Zr(1,4-diphenyl-1,3-butadiene) in 10 ml of n-hexane.

A stirred 5 liter reactor was charged with 1.6 liters of n-hexane and 1.4 liters of propylene and the mixture was maintained at a temperature of 10° C. An aliquot of the catalyst prepared as above containing 20 μmol of Zr was injected into the reactor along with 400 ml of n-hexane. The reactor contents were heated to 70° C. and after holding at 70° C. for ten minutes the reaction was stopped by transferring the contents to a sample container. After drying 585 g of free flowing polypropylene powder was obtained of bulk density 0.34 g/cm$^3$. The efficiency was calculated to be 320,723 g PE/g Zr.

Example 11

20 gram of triethylaluminum treated silica (prepared as in Example 5) was charged to a vessel. 17.2 ml of a 0.0465M solution of [(p-HOC$_6$H$_4$)B(C$_6$F$_5$)$_3$][NHMe(C$_{18-22}$H$_{37-45}$)$_2$] in toluene was treated with 8 ml of a 0.1M solution of triethylaluminum in toluene and the mixture briefly stirred. A further 10 ml of toluene was added to give a total volume of 36 ml. This solution was added to the dry triethylaluminum treated silica and the mixture was rapidly agitated. 400 ml of n-hexane was added and the resulting slurry agitated for 10 minutes. 6.15 ml of a 0.13M solution of (C$_5$Me$_4$SiMe$_2$N$^t$Bu)Ti(η$^4$-1,3-pentadiene) in Isopar™ E was added and the mixture agitated for 1 hour. This resulted in the formation of a dark green colored supported catalyst.

Isopentane, ethylene, 1-butene (if required), hydrogen and supported catalyst were continuously fed into a 10 liter jacketed, continuously stirred tank reactor and the slurry product formed was continuously removed. The total pressure was 15 bar and the temperature was maintained at 70° C. The slurry withdrawn was fed to a flash tank to remove the diluent and the dry, flee-flowing polymer powder was collected. In a first run the following feed rates were employed. Isopentane (2500 g/hr), ethylene (760 g/hr), hydrogen (1 Nl/hr) and supported catalyst 0.368 g/hr. Polymer powder was produced at an efficiency of 823,000 g PE/g Ti with the following properties. I2 2.41, density 0.9638 g/cm3. In a second run the following feed rates were employed. Isopentane (2500 g/hr), ethylene (1120 g/hr), 1-butene (37 g/hr), hydrogen (1 Nl/hr) and supported catalyst (0.325 g/hr). Polymer powder was produced at all efficiency of 1,569,000 g PE/g Ti and with the following properties, I$_2$ 1.02, density 0.9303 g/cm$^3$, 1-butene 1.72 percent.

Example 12

15 gram of triethylaluminum treated silica (prepared as in Example 5 but using a 45 micron particle size silica gel, Grace Davison) was charged to a vessel. 2 ml of a 0.298M solution of [(p-HOC$_6$H$_4$)B(C$_6$F$_5$)$_3$][NHMe(C$_{18-22}$H$_{37-45}$)$_2$] in toluene was treated with 6 ml of a 0.1M solution of triethylaluminum in toluene and the mixture briefly stirred. A further 8.5 ml of toluene was added to give a total volume of 16.5 ml. This solution was added to the dry triethylaluminum treated silica and the mixture was rapidly agitated. 400 ml of n-hexane was added and the resulting slurry agitated for 10 minutes. 4.61 ml of a 0.13M solution of (C$_5$Me$_4$SiMe$_2$N$^t$Bu)Ti(η$^4$-1,3-pentadiene) in Isopar™ E was added and the mixture agitated for 1 hour. This resulted in the formation of a dark green colored supported catalyst.

n-Hexane (2500 g/hr), ethylene (1025 g/hr), hydrogen (3.5 Nl/hr) and supported catalyst (0.5875 g/hr) were continuously fed to a 10 liter, jacketed continuously stirred tank reactor. The total pressure was 12 bar and the temperature was maintained at 65° C. The slurry withdrawn was fed to a second identical reactor along with n-hexane (2500 g/hr), ethylene (950 g/hr), 1-butene (4.7 g/hr) and supported catalyst (0.5875 g/hr). The total pressure in the second reactor was 11 bar and the temperature 75° C. The slurry withdrawn was fed to a flash tank to remove the diluent and the dry, free flowing powder polymer powder was collected. The overall efficiency was calculated to be 750,000 g PE/g Ti. The polymer powder had the following properties. I$_2$ 0.47, density 0.9679 g/cm$^3$ and bulk density 0.373 g/cm$^3$.

Figure 1B:
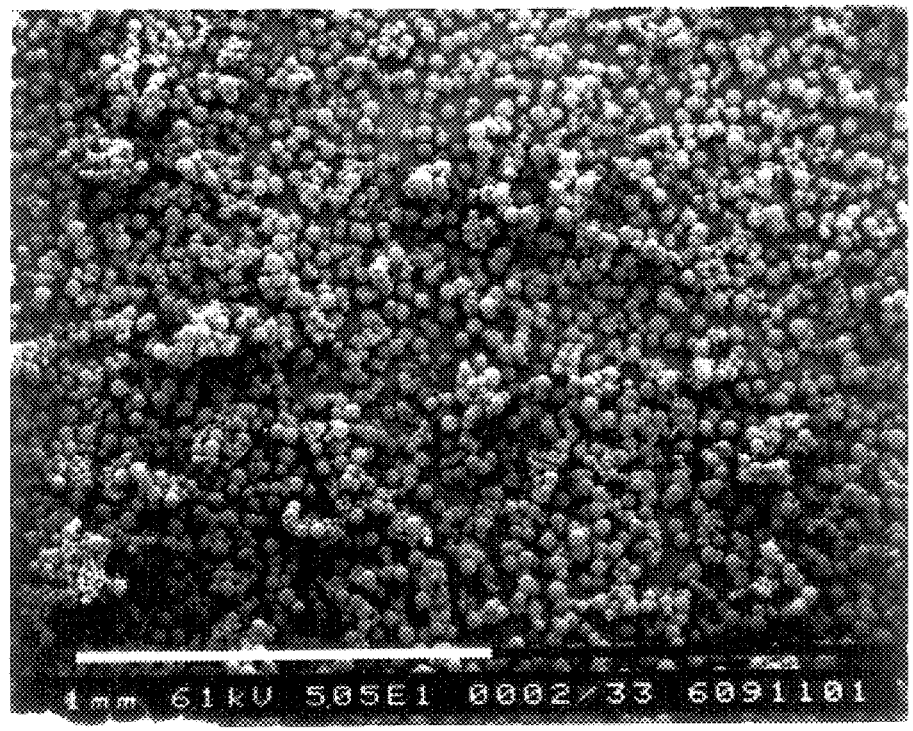
Figure 2A:
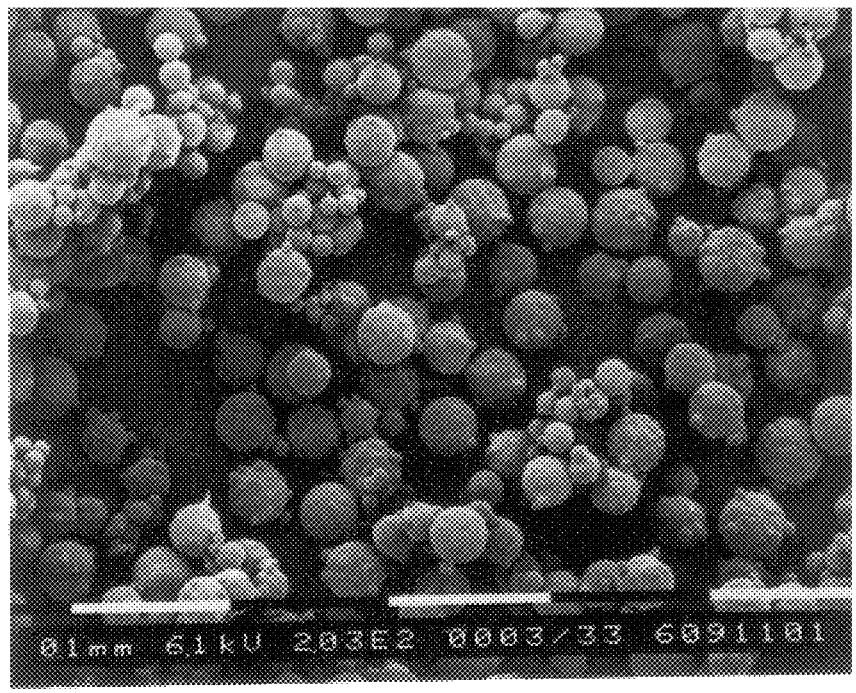
FIG. 2A and FIG. 2B are scanning electron micrographs of slurry produced polyethylene at a magnification of 200 times.
Figure 2B:
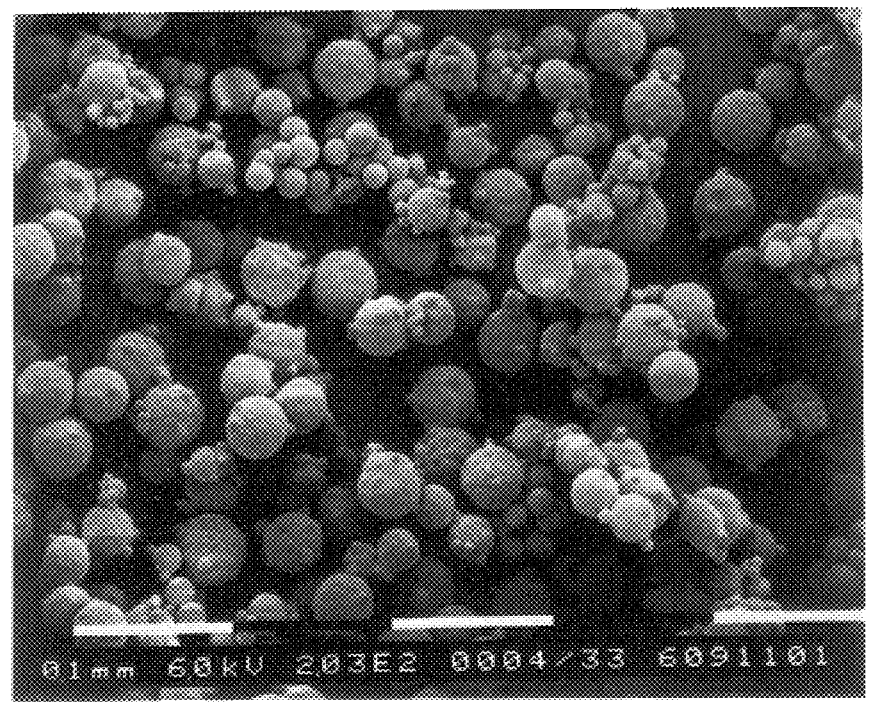
Figure 3A:
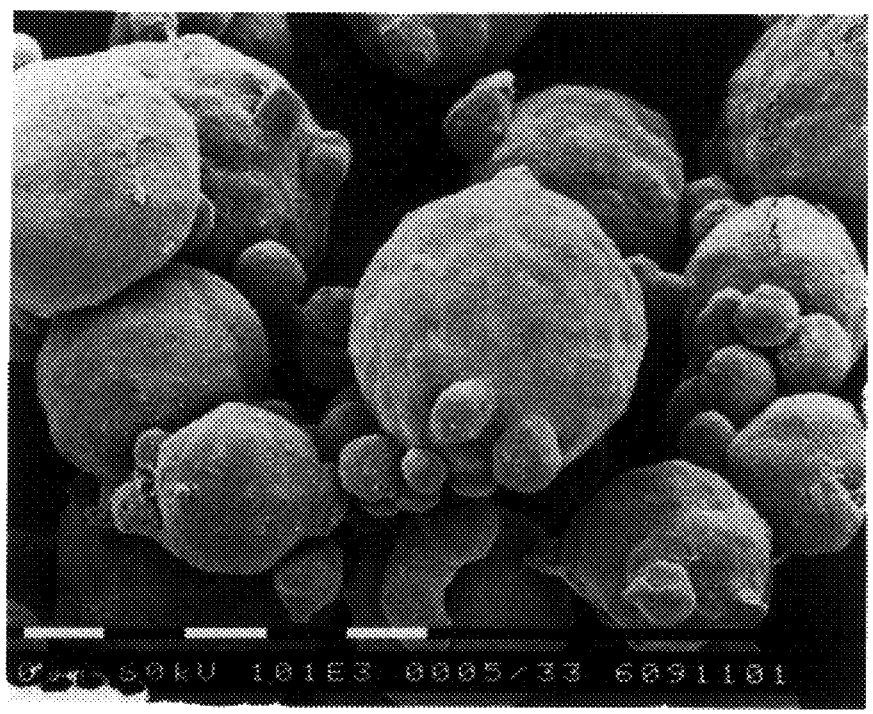
FIG. 3A and FIG. 3B are scanning electron micrographs of slurry produced polyethylene at a magnification of 1000 times.
Figure 3B:
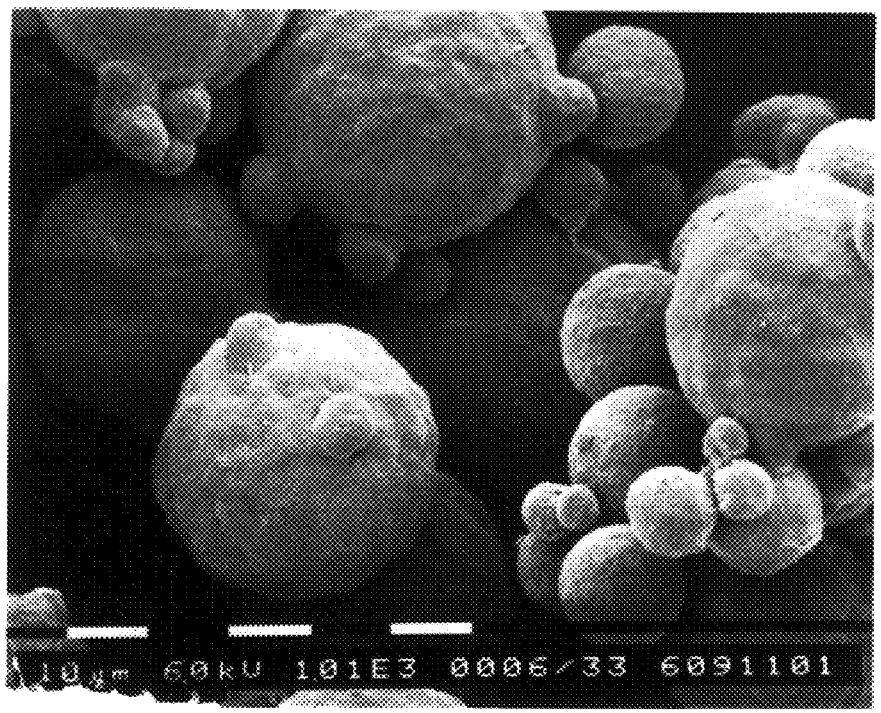

Scanning Electron Micrographs: Samples of slurry produced polyethylene (HDPE), from Example 1, which had been gold coated were examined by scanning electron micrograph using a Philips model SEM505 operating at an accelerating voltage of 6 kV, with results as shown in FIG. 1A and FIG. 1B at a magnification of 50 times, FIG. 2A and FIG. 2B at 200 times, and FIG. 3A and FIG. 3B at 1000 times. The photomicrographs indicate that the surface morphology is very smooth and that there appear to be particles of primarily two size ranges. The larger particles are in the size range of approximately 50 microns in diameter and the smaller particles are in the size range of approximately 5 microns in diameter.

Gas Phase Examples

The polymerization examples which follow were carried out in a 13 liter gas phase reactor having a four inch diameter thirty inch long fluidization zone and an eight inch diameter ten inch long velocity reduction zone which are connected by a transition section having tapered walls. Typical operating ranges were 40 to 100° C., 6 to 25 bar total pressure and up to 8 hours reaction time. Ethylene, comonomer, hydrogen and nitrogen entered the bottom of the reactor where they passed through a gas distributor plate. The flow of the gas was 2 to 8 times the minimum particle fluidization velocity. See *Fluidization Engineering,* 2nd Ed., D. Kunii and O. Levenspiel, 1991 Butterworth-Heinemann. Most of the suspended solids disengaged in the velocity reduction zone. The reactant gases exited the top of the velocity reduction zone and passed through a dust filter to remove any fines. The gases then passed through a gas booster pump. The polymer was allowed to accumulate in the reactor over the course of the reaction. The total system pressure was kept constant during the reaction by regulating the flow of monomer into the reactor. Polymer was removed from the reactor to a recovery vessel by opening a valve located at the bottom of the fluidization zone. The polymer recovery vessel was kept at a lower pressure than the reactor. The pressures of ethylene, comonomer and hydrogen reported refer to partial pressures.

The mode of reactor operation which was employed is referred to as semi-batch. The catalyst was prepared and loaded into a catalyst injector in an inert atmosphere glovebox. The injector was removed from the glovebox and inserted into the tope of the reactor. Appropriate amounts of ethylene, 1-butene, hydrogen and nitrogen were introduced into the reactor to bring the total pressure to the desired reaction temperature. The catalyst was then injected and the polymer was usually allowed to form for 30 to 90 minutes. The total system pressure was kept constant during the reaction by regulating the flow of monomer into the reactor. Upon completion of the run the reactor was emptied and the polymer powder was collected.

Example 13

Catalyst/support Preparation 15.9 grams of Crosfield type ES70Y silica (surface area= 315 m$^2$/g and a Malvern particle size [D50]=106.8 micron) was heated at 500° C. for 4 hours in an inert stream of nitrogen. The silica was allowed to cool to room temperature in an inert stream of nitrogen. The silica calcination tube was then sealed at both ends and brought into an inert atmosphere glovebox. The silica was removed from the calcination tube then slurried with 80 ml of hexane at a ratio of 5 ml hexane/gram silica. To the slurried silica was added 2.93 grams of a 93 weight percent solution of triethylaluminum (TEA) which corresponded to a treatment of 1.5 mmoles TEA/gram silica. The slurry was allowed to sit for 2 hours with gentle agitation by hand every 15 to 20 minutes. After 2 hours the silica was filtered and washed twice with a total of 100 ml of hexane to remove any soluble aluminum compounds which may have resulted during the TEA treatment step. The silica was then dried at room temperature under vacuum to give a free-flowing powder.

To 100 ml of a 0.036 M solution of [(p-HOC$_6$H$_4$)B (C$_6$F$_5$)$_3$][NHMe(C$_{18-22}$H$_{37-45}$)$_2$] in toluene was added 0.0036 moles (0.383 grams) of TEA. The mixture was stirred at room temperature for 18½ hours. 0.278 ml of the preceding solution was added dropwise to 1.0 gram of the TEA treated ES70Y silica described previously followed by vigorous shaking for 15 minutes. 0.0427 ml of a 0.234 M solution of ($\eta^5$-C$_5$Me$_4$SiMe$_2$N$^t$Bu)Ti($\eta^4$-1,3-pentadiene) was then added dropwise to the silica followed by vigorous shaking for 15 minutes. The catalyst loading was 10 micromol/gram silica. To the formulated catalyst was added 10 ml of hexane followed by vigorous shaking of the resulting slurry for 20 minutes. The slurry was then filtered and washed twice with a total of 10 ml of hexane. The formulated catalyst was then dried at room temperature under vacuum to give a free-flowing powder.

Polymerization 0.1 grams of the formulated catalyst described above was added to the semi-batch gas phase reactor which was under an ethylene pressure of 6.5 bar, a 1-butene pressure of 0.14 bar, a hydrogen pressure of 0.04 bar and a nitrogen pressure of 2.8 bar. The temperature of polymerization throughout the run was 70° C. A 6° C. exotherm was measured upon injection of the catalyst. 16.0 grams of polymer were recovered after 30 minutes.

Example 14

0.075 grams of the formulated catalyst described in Example 13 was added to the semi-batch gas phase reactor which was under an ethylene pressure of 6.5 bar, a 1-butene pressure of 0.14 bar, a hydrogen pressure of 0.04 bar and a nitrogen pressure of 2.8 bar. The temperature of polymerization throughout the run was 70° C. A 6° C. exotherm was measured upon injection of the catalyst. 15.9 grams of polymer were recovered after 30 minutes.

Example 15

0.05 grams of the formulated catalyst described in Example 13 was mixed with 0.415 grams of the TEA treated silica described in Example 13. The mixture was added to the semi-batch gas phase reactor which was under an ethylene pressure of 6.5 bar, a 1-butene pressure of 0.14 bar, a hydrogen pressure of 0.04 bar and a nitrogen pressure of 2.8 bar. The temperature of polymerization throughout the run was 69° C. A 5° C. exotherm was measured upon injection of the catalyst. 5.4 grams of polymer were recovered after 18 minutes.

Example 16

0.05 grams of the formulated catalyst described in Example 13 was mixed with 0.4 grams of the TEA treated silica described in Example 13. The mixture was added to the semi-batch gas phase reactor which was under an ethylene pressure of 6.5 bar, a 1-butene pressure of 0.14 bar, a hydrogen pressure of 0.04 bar and a nitrogen pressure of 13.7 bar. The catalyst was injected at a reactor temperature of 70° C. A 4° C. exotherm was measured upon injection of the catalyst. Following injection of the catalyst the temperature in the reactor rose to 75° C. over the course of 90 minutes. 24.3 grams of polymer were recovered after 90 minutes.

Example 17

Catalyst Preparation

To 100 ml of a 0.036 M solution of [(p-HOC$_6$H$_4$)B (C$_6$F$_5$)$_3$][NHMe(C$_{18-22}$H$_{37-45}$)$_2$] in toluene was added 0.0036 moles (0.383 grams) of TEA. The mixture was allowed to stir at room temperature for 18½ hours. 0.417 ml of the preceding solution was added dropwise to 1.0 gram of the TEA treated ES70Y silica described previously in Example 13 followed by vigorous shaking for 15 minutes. 0.0641 ml of a 0.234 M solution of ($\eta^5C_5Me_4SiMe_2N^tBu$)Ti($\eta^4$-1,3-pentadiene) was then added dropwise to the silica followed by vigorous shaking for 15 minutes. The catalyst loading was 15 micromol/gram silica. To the formulated catalyst was added 10 ml of hexane followed by vigorous shaking of the resulting slurry for 20 minutes. The slurry was then filtered and washed twice with a total of 10 ml of hexane. The formulated catalyst was then dried at room temperature under vacuum to give a free-flowing powder.

Polymerization 0.033 grams of the formulated catalyst described above was mixed with 0.35 grams of the TEA treated silica described in Example 13. The mixture was added to the semi-batch gas phase reactor which was under an ethylene pressure of 6.5 bar a 1-butene pressure of 0.14 bar and a nitrogen pressure of 13.7 bar. The temperature of polymerization throughout the run was 72° C. No exotherm was measured upon injection of the catalyst. 5.8 grams of polymer were recovered after 15 minutes.

Example 18

0.017 grams of the formulated catalyst described in Example 5 was mixed with 0.35 grams of the TEA treated silica described in Example 1. The mixture was added to the semi-batch gas phase reactor which was under an ethylene pressure of 6.5 bar, a 1-butene pressure of 0.14 bar, a hydrogen pressure of 0.04 bar and a nitrogen pressure of 13.7 bar. The catalyst was injected at a reactor temperature of 71° C. No exotherm was measured upon injection of the catalyst. 12.5 grams of polymer were recovered after 90 minutes.

Example 19

Catalyst Preparation

To 100 ml of a 0.036 M solution of [(p-HOC$_6$H$_4$)B(C$_6$F$_5$)$_3$][NHMe(C$_{18-22}$H$_{37-45}$)$_2$] in toluene was addled 0.0036 moles (0.383 grams) of TEA. The mixture was allowed to stir at room temperature for 18½ hours. 0.278 ml of the preceding solution was added dropwise to 1.0 gram of a TEA treated Crosfield type ES70 silica (surface area=289 m$^2$/g and a Malvern particle size [D50]=35.2 micron) followed by vigorous shaking for 15 minutes. The Crosfield type ES70 silica had been calcined and treated with TEA in a manner analogous to the procedure described in Example 1. 0.0427 ml of a 0.234 M solution of ($\eta^5C_5Me_4SiMe_2N^tBu$)—Ti($\eta^4$-1,3-pentadiene) was then added dropwise to the silica followed by vigorous shaking for 15 minutes. The catalyst loading was 10 mmol/gram silica. To the formulated catalyst was added 10 ml of hexane followed by vigorous shaking of the resulting slurry for 20 minutes. The slurry was then filtered and washed twice with a total of 10 ml of hexane. The formulated catalyst was then dried at room temperature under vacuum to give a free-flowing powder.

Polymerization 0.05 grams of the formulated catalyst described above was mixed with 0.35 grams of the TEA treated silica described in Example 13. The mixture was added to the semi-batch gas phase reactor which was under an ethylene pressure of 6.5 bar, a 1-butene pressure of 0.14 bar, a hydrogen pressure of 0.04 bar and a nitrogen pressure of 13.7 bar. The temperature of polymerization throughout the run was 72° C. A 3° C. exotherm was measured upon injection of the catalyst. 26.3 grams of polymer were recovered after 90 minutes.

III. Polypropylene Examples

Example 20

Catalyst Preparation

Regarding various aspects of the preparation of the transition metal compound, See *Organomet* 13, (1994), 954 at page 962; see also U.S. Pat. No. 5,278,264 hereby incorporated herein by reference:

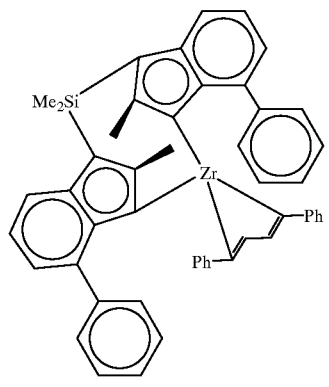

24Dn
Me$_2$Si bis(2-Me-4-Ph-Indenyl) Zr diphenyl butadiene rac-Me$_2$Si(2-methyl-4-phenyl-indenyl)$_2$ZrCl$_2$ (4.00 g, 6.36 mmol) and diene (1.312 g, 6.36 mmol) were weighed into a 250 mL flask and slurried into 150 mL of octane. 8.9 mL of nBuLi (1.6 M, 14.31 mmol) was added via syringe. The reaction mixture was stirred at room temperature over the weekend. The reaction was then held at 80–85° C. for approximately 6 hours followed by 2 hours at reflux, then cooled to room temperature. The octane solution was filtered after cooling and the insolubles were washed with hexane until colorless. The solvent was removed in vacuo. The product was slurried into 10 ml fresh hexane and placed in the freezer at −30° F. for 1 hour. The cold slurry was filtered and the solid product dried in vacuo, giving rac-Me$_2$Si(2-methyl-4-phenyl-indenyl)$_2$Zr(1,4-diphenyl-1,3-butadiene) as a red solid (yield=2.182 g, 45 percent; 82.3 weight percent 24DN, 17.7 weight percent free diene). 1H NMR (C$_6$D$_6$, ppm): 7.8–6.5 (multiplets, aromatic protons, and free diene protons), 5.6 (s, 2H, indenyl proton), 3.45 (multiplet, 2H, PhC4H4Ph) 1.7 (singlet overlapping multiplet, s, indenyl methyl; m, PhC$_4$H$_4$Ph, total 8H), 0.9 (s, SiMe$_2$, 6H).

Pretreatment of the silica: To 5.00 g 50 μm silica (Grace Davison XPO-2402, which had previously been calcined at 500° C.) was added 50 mL toluene. To the mixture, 5 mL of neat triethylaluminum (TEA) were added, and the mixture was stirred for one hour. The mixture was filtered over a medium frit, and the silica was washed twice with 50 mL boiling toluene, followed by 50 mL hexane. The silica was then pumped dry by closure of the frit top with a stopper. After 3 hours 45 minutes in vacuo, 5.48 g of treated silica (SiO$_2$/TEA) was recovered.

A solution of 0.91 mL of 0.1 M of [(p-HOC$_6$H$_4$)B(C$_6$F$_5$)$_3$][NHMe(C$_{18-22}$H$_{37-45}$)$_2$] in toluene (91 μmoles) was combined with 2.7 mL of toluene and 0.91 mL of 0.1 M triethylaluminum (TEA, 91 μmoles) and the solution with a total volume of 4.5 mL was stirred for 10 minutes. This solution was added in three portions to 2.28 g of the pretreated SiO$_2$ prepared above in a 50 mL flask. The mixture was gently mixed for several minutes with a spatula to evenly distribute the liquid over the solid until a free flowing powder was obtained. 20 mL of hexane was added to the solid, mixing the new mixture with a spatula for 2 minutes. The pretreated silica was filtered and pumped dry for one hour. 2.33 g solid product was obtained and placed in a 100 mL vessel. A solution of 85 mg of 24Dn transition metal compound prepared above was dissolved in 3.6 mL of toluene (91 µmoles) and added to the vessel in 3 portions of about 1.2 mL each, gently mixing thoroughly after each portion had been added with a spatula to ensure homogeneous distribution of the catalyst solution on the solid. The solid material was rinsed four times with 40 mL hexane. The grayish-blue solid was dried in vacuo one hour. A sample of 127 mg of this finished material was submitted for Zr analysis by neutro activation. The analysis showed that the loading was 23 µmoles of Zr/g silica.

Example 21

Preparation of the pretreated support. Crosfield silica ES70 was calcined at 250° C. for four hours with nitrogen flow through a fluidized bed. After cooling, to 5 g of the calcined silica in a 4 oz bottle were added 50 mL hexane and 5 mL of neat TEA. The bottle was closed and rocked for an hour on a rocker type mixer. The sample was vacuum dried for one hour to give 5.3 g of finished TEA-treated silica.

A solution of 0.6 mL of 0.1 M of [(p-HOC$_6$H$_4$)B(C$_6$F$_5$)$_3$][NHMe(C$_{18-22}$H$_{37-45}$)$_2$] in toluene (60 µmoles) was combined with 0.3 mL of toluene and 0.0.6 mL of 0.1 M triethylaluminum (TEA, 60 µmoles) and the solution with a total volume of 1.5 mL was stirred for 10 minutes. This solution was added in three portions to 1.0 g of the pretreated SiO$_2$ prepared above in a 100 mL bottle. The mixture was gently mixed for several minutes with a spatula to evenly distribute the liquid over the solid until a free flowing powder was obtained, at which point it was washed three times with 20 mL portions of hexane. The pretreated silica, was filtered and pumped dry for one hour. The solid product was placed in a 100 mL vessel. A 1.5 mL solution containing 60 µmoles of 24Dn transition metal compound was added to the vessel, gently mixing thoroughly with a spatula to ensure homogeneous distribution of the catalyst solution on the solid.

General Polymerization Procedure

Propylene, Isopar™ E, hydrogen, hexane and nitrogen were all purified by passage through packed columns of activated Q-5 and alumina. The supported 24Dn catalyst was slurried in the glove box with about 20 mL of hexane.

Polypropylene Prepared With Supported Catalyst from Example 20

A two-liter stainless steel reactor was dried by vigorous stirring of 1 ml 0.1 M triisobutyl aluminum solution in toluene added to 1 liter Isopar™ for one hour at 70° C. The reactor was washed with Isopar™ at 70° C. It was then charged with a mixture consisting of 351 g of propylene, 40 g of hexane, and 26 delta psi hydrogen by differential pressure expansion from a 75 mL tank.

The mixture was heated to 70° C. and then a slurry prepared with 100 mg (2 µmoles 24Dn catalyst as Zr), 10 µmoles TEA and 5 ml hexane was added to the reactor. The reaction was allowed to proceed for 30 minutes. The contents of the reactor were then collected in a nitrogen purged stainless steel container. The polymers were dried overnight in a vacuum oven at 130° C. Yield 48 g. Standard 13C techniques showed that the polymer was 96 percent triad [mm] isotactic, with 0.95 percent inverse insertions. The polymer had Mw/Mn=320,000/82.000=3.9, as determined by standard GPC techniques.

Polypropylene Prepared With Supported Catalyst from Example 21

Same procedure as described above was repeated, using 351 g of propylene, 40 g of hexane, and 26 delta psi hydrogen by differential pressure expansion from a 75 ml tank. After 35 minutes of reaction time, the polymer was collected and dried as described above. The yield of polypropylene was 45 g.

Solubility of Ionic Compounds

| Compound | Note | Solvent | Solubility at 22° C. mol/liter | Solubility at 22° C. weight percent |
|---|---|---|---|---|
| [NHMe(C$_{18-22}$H$_{37-45}$)$_2$][HOC$_6$H$_4$B(C$_6$F$_5$)$_3$] | 1 | toluene | >0.3 | >28.2 |
| [NEt$_3$H][HOC$_6$H$_4$B(C$_6$F$_5$)$_3$] | 2 | toluene | <0.001 | <0.08 |
| [NHMe(C$_{18-22}$H$_{37-45}$)$_2$][HOC$_6$H$_4$B(C$_6$F$_5$)$_3$] | 3 | n-hexane | 0.014 | 2.37 |
| [NHMe(C$_{18-22}$H$_{37-45}$)$_2$][B(C$_6$F$_5$)$_4$] | 4 | n-hexane | >0.34 | >38.8 |
| [NHMe(C$_{18-22}$H$_{37-45}$)$_2$][HOC$_6$H$_4$B(C$_6$F$_5$)$_3$] + TEA | 5 | toluene | >0.3 | >28 |
| [NHMe(C$_{18-22}$H$_{37-45}$)$_2$][HOC$_6$H$_4$B(C$_6$F$_5$)$_3$] + TEA | 6 | n-hexane | 0.0024 | 0.45 |

1) The influence of the long hydrocarbon chain ammonium cation on the toluene solubility of the hydroxyborate anion is evidenced by comparing 1 and 2.
2) The hexane solubility of [(p-HOC$_6$H$_4$)B(C$_6$F$_5$)$_3$][NHMe(C$_{18-22}$H$_{37-45}$)$_2$] is much less than the toluene solubility (compare 1 and 3).
3) The influence of the hydroxy substituent on the solubilities of the long chain ammonium salts is evidenced by comparing 3 and 4.
4) The influence of solvent on the solubilities of the product of [(p-HOC$_6$H$_4$)B(C$_6$F$_5$)$_3$][NHMe(C$_{18-22}$H$_{37-45}$)$_2$] and TEA is evidenced by comparing 5 and 6. Note that 6 is even more insoluble than 3.

What is claimed is:

1. A compound that is the reaction product of:
   (a) an ionic compound comprising (a)(1) a cation and (a)(2) an anion having up to 100 nonhydrogen atoms and containing at least one substituent comprising a moiety having an active hydrogen,
   wherein the cation (a)(1) is represented by the following general formula: [L*—H]$^+$, wherein:
   L* is a nitrogen, oxygen, sulfur or phosphorus containing Lewis base containing from one to three C$_{10-40}$ alkyl groups with a total of from 12 to 100 carbons, and the anion (a)(2) corresponds to Formula (II):

wherein:
   M' is a metal or metalloid selected from Groups 5–15 of the Periodic Table of the Elements;
   Q independently in each occurrence is selected from the group consisting of hydride, dihydrocarbylamido, halide, hydrocarbyloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion in each of these groups preferably having from 1 to 20 carbons, with the proviso that in not more than one occurrence is Q halide; G is a polyvalent hydrocarbon radical having r+1 valencies bonded to M' and r groups (T—H);

the group (T—H) is a radical wherein T comprises O, S, NR, or PR, the O, S, N or P atom of which is bonded to hydrogen atom H wherein R is a hydrocarbyl radical, a trihydrocarbylsilyl radical, a trihydrocarbyl germyl radical or hydrogen;

m is an integer from 1 to 7;

n is an integer from 0 to 7;

q is an integer of 0 or 1;

r is an integer from 1 to 3;

z is an integer from 1 to 8;

d is an integer from 1 to 7; and n+z−m=d, and (c) an organometal or metalloid compound corresponding to the formula:

$$M^oR^c_xX^a_y,$$

wherein $M^o$ is a metal or metalloid selected from Groups 2, 12, 13 or 14 of the Periodic Table of the Elements, $R^c$ independently each occurrence is hydrogen or a group having from 1 to 80 nonhydrogen atoms which is hydrocarbyl, hydrocarbylsilyl, trihydrocarbylsilyl, trihydrocarbylgermyl or hydrocarbylsilylhydrocarbyl;

$X^a$ is a noninterfering group having from 1 to 100 nonhydrogen atoms which is halo-substituted hydrocarbyl, hydrocarbylamino-substituted hydrocarbyl, hydrocarbyloxy-substituted hydrocarbyl, hydrocarbylamino, di(hydrocarbyl) amino, hydrocarbyloxy or halide;

x is a nonzero integer which may range from 1 to an integer equal to the valence of $M^o$;

y is zero or a nonzero integer which may range from 1 to an integer equal to 1 less than the valence of $M^o$; and x+y equals the valence of $M^o$.

2. The catalyst component dispersion of claim 1, wherein the catalyst component further comprises (b) a transition metal compound and wherein the catalyst component is a substantially inactive catalyst precursor; or wherein the catalyst component further comprises (c) an organometal or metalloid compound wherein the metal or metalloid is selected from the Groups 1–14 of the Periodic Table of the Elements and the catalyst component is a reaction product of (a) and (c).

3. The catalyst component dispersion of claim 1, characterized by an average particle size of (a), as measured by laser diffraction, in the range of from 0.1 to 200 μm.

4. The catalyst component dispersion of claim 1, wherein the anion (a)(2) corresponds to Formula (II):

$$[M'^{m+}Q_n(G_q(T—H)_r)_z]^{d-} \quad (II)$$

wherein:

M' is a metal or metalloid selected from Groups 5–15 of the Periodic Table of the Elements;

Q independently in each occurrence is selected from the group consisting of hydride, dihydrocarbylaimdo, halide, hydrocarbyloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion in each of these groups preferably having from 1 to 20 carbons, with the proviso that in not more than one occurrence is Q halide; G is a polyvalent hydrocarbon radical having r+1 valencies bonded to M' and r groups (T—H);

the group (T—H) is a radical wherein T comprises O, S, NR, or PR, the O, S, N or P atom of which is bonded to hydrogen atom H wherein R is a hydrocarbyl radical, a trihydrocarbylsilyl radical, a trihydrocarbyl germyl radical or hydrogen;

m is an integer from 1 to 7;

n is an integer from 0 to 7;

q is an integer of 0 or 1;

r is an integer from 1 to 3;

z is an integer from 1 to 8;

d is an integer from 1 to 7; and n+z−m=d.

5. The catalyst component dispersion of claim 4, wherein in the anion (a)(2) the at least one substituent comprising a moiety having an active hydrogen corresponds to Formula (I):

$$G_q(T—H)_r \quad (I)$$

wherein G is a polyvalent hydrocarbon radical, the group (T—H) is a radical wherein T comprises O, S, NR, or PR, the O, S, N, or P atom of which is bonded to hydrogen atom H, wherein R is a hydrocarbyl radical, a trihydrocarbylsilyl radical, a trihydrocarbyl germyl radical or hydrogen, H is hydrogen, q is 0 or 1, and r is an integer from 1 to 3.

6. The catalyst component dispersion of claim 1, wherein the cation (a)(1) is selected from the group consisting of Bronsted acidic cations, carbonium cations, silylium cations, oxonium cations, organometallic cations and cationic oxidizing agents.

7. The catalyst component dispersion of claim 6, wherein the cation (a)(1) of ionic compound (a) is represented by the following general formula: $[L^*—H]^+$, wherein:

$L^*$ is a nitrogen, oxygen, sulfur or phosphorus containing Lewis base containing from one to three $C_{10-40}$ alkyl groups with a total of from 12 to 100 carbons.

8. The catalyst component dispersion of claim 7, wherein the cation (a)(1) of ionic compound (a) is represented by the following general formula: $[L^*—H]^+$, wherein:

$L^*$ is a nitrogen, oxygen, sulfur or phosphorus containing Lewis base containing from one to three $C_{10-40}$ alkyl groups with a total of from 12 to 100 carbons, and the anion (a)(2) is tris(pentafluorophenyl)(4-hydroxyphenyl)borate.

9. The catalyst component dispersion of claim 1 in dry particulate form produced by removal of the diluent.

10. A supported solid catalyst comprising (a) an ionic compound comprising (a)(1) a cation and (a)(2) an anion having up to 100 nonhydrogen atoms and the anion containing at least one substituent comprising a moiety having an active hydrogen, (b) a transition metal compound, (c) an organometal or metalloid compound wherein the metal or metalloid is selected from the Groups 1–14 of the Periodic Table of the Elements, and (d) a support material, wherein, (i) the support material is a pretreated support material and in the supported catalyst component the anion (a)(2) is not chemically bonded to the support (d), or (ii) the ionic compound has a solubility in toluene at 22° C. of at least 0.1 weight percent, the support material used is a support material containing tethering groups and in the supported catalyst component the anion (a)(2) is chemically bonded to the support (d); and, wherein the solid catalyst is obtained by combining components (a), (b), (c), and (d) in any order, and wherein, during at least one step in the preparation of the solid catalyst, component (a) is dissolved in a diluent in which (a) is soluble, optionally in the presence of one or more of components (b), (c), and (d) or the contact product of (a) with such one or more of (b), (c), and (d), and then is converted into solid form.

11. The supported solid catalyst of claim 10, wherein, during the preparation of the solid catalyst, a dispersion comprising component (a) is generated by cooling a solution of (a) in a diluent in which (a) is soluble, by contacting a solution of (a) in a diluent in which (a) is soluble with a diluent in which (a) is insoluble or sparingly soluble, by evaporating diluent from a solution of (a), by adding one or more precipitating agents to a solution of (a), or a combination of two or more of these techniques.

12. The supported solid catalyst of claim 11 wherein, during the preparation of the solid catalyst, a dispersion comprising component (a) in solid form is generated by contacting a solution of (a) in a diluent in which (a) is soluble, optionally in the presence of one or more of components (b), (c), and (d) or the contact product of (a) with one or more of (b), (c), and (d), with a diluent in which (a) is insoluble or sparingly soluble.

13. The supported solid catalyst of claim 10, wherein the anion (a)(2) corresponds to Formula (II):

wherein:

M' is a metal or metalloid selected from Groups 5–15 of the Periodic Table of the Elements;

Q independently in each occurrence is selected from the group consisting of hydride, dihydrocarbylamido, halide, hydrocarbyloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion in each of these groups preferably having from 1 to 20 carbons, with the proviso that in not more than one occurrence is Q halide; G is a polyvalent hydrocarbon radical having r+1 valencies bonded to M' and r groups (T—H);

the group (T—H) is a radical wherein T comprises O, S, NR, or PR, the O, S, N or P atom of which is bonded to hydrogen atom H wherein R is a hydrocarbyl radical, a trihydrocarbylsilyl radical, a trihydrocarbyl germyl radical or hydrogen;

m is an integer from 1 to 7;
n is an integer from 0 to 7;
q is an integer of 0 or 1;
r is an integer from 1 to 3;
z is an integer from 1 to 8;
d is an integer from 1 to 7; and
n+z−m=d.

14. The supported solid catalyst of claim 13, wherein in the anion (a)(2) the at least one substituent comprising a moiety having an active hydrogen corresponds to Formula (I):

wherein G is a polyvalent hydrocarbon radical, the group (T—H) is a radical wherein T comprises O, S, NR, or PR, the O, S, N, or P atom of which is bonded to hydrogen atom H, wherein R is a hydrocarbyl radical, a trihydrocarbylsilyl radical, a trihydrocarbyl germyl radical or hydrogen, H is hydrogen, q is 0 or 1, and r is an integer from 1 to 3.

15. The supported solid catalyst of one of claims 10, wherein the cation (a)(1) is selected from the group consisting of Bronsted acidic cations, carbonium cations, sylium cations, oxonium cations, organometallic cations and cationic oxidizing agents.

16. The supported solid catalyst of claim 15, wherein the cation (a)(1) of ionic compound (a) is represented by the following general formula: [L*—H]+, wherein:

L* is a nitrogen, oxygen, sulfur or phosphorus containing Lewis base containing from one to three $C_{10-40}$ alkyl groups with a total of from 12 to 100 carbons.

17. The supported solid catalyst of claim 16, wherein the cation (a)(1) of ionic compound (a) is represented by the following general formula: [L*—H]+, wherein:

L* is a nitrogen, oxygen, sulfur or phosphorus containing Lewis base containing from one to three $C_{10-40}$ alkyl groups with a total of from 12 to 100 carbons, and the anion (a)(2) is tris(pentafluorophenyl)(4-hydroxyphenyl)borate.

18. The supported solid catalyst of claim 10, wherein the organometal or metalloid compound corresponds to the formula $AlR^o_x$, wherein $R^o$ independently in each occurrence is hydrogen or a hydrocarbyl radical having from 1 to 20 carbon atoms, and x is 3.

19. A method for preparing a dispersion of a supported catalyst component comprising (a) an ionic compound comprising (a)(1) a cation and (a)(2) an anion having up to 100 nonhydrogen atoms and the anion containing at least one substituent comprising a moiety having an active hydrogen, and (d) a support material, where the supported catalyst component is in solid form dispersed in a diluent in which both (a) and (d) are insoluble or sparingly soluble, the method comprising converting a solution of the ionic compound (a) in a diluent in which (a) is soluble in the presence of the support material into a dispersion comprising component (a) in solid form, and wherein, (i) the support material used is a pretreated support material and, in the supported catalyst component, the anion (a)(2) is not chemically bonded to the support (d), or (ii) the ionic compound used has a solubility in toluene at 22° C. of at least 0.1 weight percent, the support material used is a support material containing tethering groups and, in the supported catalyst component, the anion (a)(2) is chemically bonded to the support (d).

20. The method of claim 19, wherein the converting is done in the presence of (b) a transition metal compound and wherein the catalyst component is a substantially inactive catalyst percursor; or wherein the converting is done in the presence of (c) an organometal or metalloid compound wherein the metal or metalloid is selected from the Groups 1–14 of the Periodic Table of the Elements and the catalyst component is a reaction product of (a) and (c).

21. The method of claim 19, wherein the dispersion comprising component (a) is generated by cooling a solution of (a) in a diluent in which (a) is soluble, by contacting a solution of (a) in a diluent in which (a) is soluble with a diluent in which (a) is insoluble or sparingly soluble, by evaporating diluent from a solution of (a), by adding one or more precipitating agents to a solution of (a), or a combination of two or more of these techniques.

22. The method of claim 21, wherein the dispersion comprising component (a) is generated by contacting a solution of (a) in a diluent in which (a) is soluble with a diluent in which (a) is insoluble or sparingly soluble.

23. The method of one of claims 22, wherein the diluent in which (a) is soluble is selected from the group consisting of toluene, benzene, and xylenes, and the diluent in which (a) is insoluble or sparingly soluble is selected from the group consisting of pentane, hexane, heptane, and octane.

24. The method of claim 19, wherein the anion (a)(2) corresponds to Formula (II):

 (II)

wherein:

M' is a metal or metalloid selected from Groups 5–15 of the Periodic Table of the Elements;

Q independently in each occurrence is selected from the group consisting of hydride, dihydrocarbylamido, halide, hydrocarbyloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion in each of these groups preferably having from 1 to 20 carbons, with the proviso that in not more than one occurrence is Q halide; G is a polyvalent hydrocarbon radical having r+1 valencies bonded to M' and r groups (T—H);

the group (T—H) is a radical wherein T comprises O, S, NR, or PR, the O, S, N or P atom of which is bonded to hydrogen atom H wherein R is a hydrocarbyl radical, a trihydrocarbylsilyl radical, a trihydrocarbyl germyl radical or hydrogen;

m is an integer from 1 to 7;

n is an integer from 0 to 7;

q is an integer of 0 or 1;

r is an integer from 1 to 3;

z is an integer from 1 to 8;

d is an integer from 1 to 7; and n+z−m=d.

25. The method of claim 24, wherein the cation (a)(1) of ionic compound (a) is represented by the following general formula: [L*—H]$^+$, wherein:

L* is a nitrogen, oxygen, sulfur or phosphorus containing Lewis base containing from one to three $C_{10-40}$ alkyl groups with a total of from 12 to 100 carbons, and the anion (a)(2) is tris(pentafluorophenyl)(4-hydroxyphenyl)borate.

26. The method of claim 19 further comprising removal of the diluent to produce the catalyst component in dry particulate form.

27. A method for preparing a solid catalyst comprising combining, in any order, (a) an ionic compound comprising (a)(1) a cation and (a)(2) an anion having up to 100 nonhydrogen atoms and the anion containing at least one substituent comprising a moiety having an active hydrogen, (b) a transition metal compound, (c) an organometal or metalloid compound wherein the metal or metalloid is selected from the Groups 1–14 of the Periodic Table of the Elements, and (d) a support material, wherein during at least one step in the preparation of the solid catalyst, component (a) is dissolved in a diluent in which (a) is soluble to produce a solution of (a), optionally in the presence of one or more of components (b), (c), and (d) or the contact product of (a) with such one or more of (b), (c), and (d), and then is converted into solid form, optionally followed by recovering the solid catalyst in dry particulate form, wherein, (i) the support material used is a pretreated support material and in the supported catalyst the anion (a)(2) is not chemically bonded to the support (d), or (ii) the ionic compound used has a solubility in toluene at 22° C. of at least 0.1 weight percent, the support material used is a support material containing tethering groups and in the supported catalyst the anion (a)(2) is chemically bonded to the support (d).

28. The method of claim 27, wherein the support material used is a pretreated support material with a pore volume of from 0.1 to 5 cm$^3$/g and in the supported catalyst the anion (a)(2) is not chemically bonded to the support (d), and wherein the volume of the solution of (a), optionally in the presence of one or both of (b) and (c), is from 20 volume percent to 200 volume percent of the total pore volume of the support material used.

29. The method of claim 27, wherein the support material used is a pretreated support material with a pore volume of from 0.1 to 5 cm$^3$/g and in the supported catalyst the anion (a)(2) is not chemically bonded to the support (d), and wherein the volume of the solution of (a), optionally in the presence of one or both of (b) and (c), is greater than 200 volume percent of the total pore volume of the support material used.

30. The method of one of claims 27, wherein the solution of (a) is produced in the presence of (b).

31. The method of one of claims 27, wherein the solution of (a) is produced in the presence of (c).

32. The method of one of claims 27, wherein the solution of (a) is produced in the presence of (b) and (c).

33. The method of one of claims 27, wherein the solid catalyst is produced by adding the solution of (a), optionally containing one or both of (b) and (c), to substantially dry pretreated support material, followed by removal of the diluent.

34. The method of claim 27 wherein during the at least one step in the preparation of the solid catalyst, a dispersion comprising component (a) in solid form is generated by cooling a solution of (a) in a diluent in which (a) is soluble, by contacting a solution of (a) in a diluent in which (a) is soluble with a diluent in which (a) is insoluble or sparingly soluble, by evaporating diluent from a solution of (a), by adding one or more precipitating agents to a solution of (a), or a combination of two or more of these techniques.

35. The method of one of claims 27, wherein component (d) is added during one of the steps in the preparation of the solid catalyst.

36. The method of one of claims 27, wherein the diluent in which (a) is soluble is selected from the group consisting of toluene, benzene, and xylenes, and the diluent in which (a) is insoluble or sparingly soluble is selected from the group consisting of pentane, hexane, heptane, and octane.

37. A method for activating a substantially inactive catalyst precursor to form a catalyst suitable for addition polymerization wherein a substantially inactive catalyst precursor comprising (a) an ionic compound comprising (a)(1) a cation and (a)(2) an anion having up to 100 nonhydrogen atoms and the anion containing at least one substituent comprising a moiety having an active hydrogen, (b) a transition metal compound, and (d) a support material, is contacted with (c) an organometal or metalloid compound, where the metal or metalloid is selected from Groups 1–14 of the Periodic Table of the Elements, to form an active catalyst.

38. The method of claim 37 wherein one or more of (a),(b) and (d), and the organometal or metalloid compound (c) are separately added into an addition polymerization reactor containing addition polymerizable monomer or monomers.

39. The method of claim 37 wherein a dispersion of a solid substantially inactive catalyst precursor, comprising (a),(b) and (d), and the organometal or metalloid compound (c) are each separately added into an addition polymerization reactor containing addition polymerizable monomer or monomers.

40. The method of one of claims 37, wherein the addition polymerization reactor is operated under slurry phase or gas phase polymerization conditions.

41. The method of claim 40, wherein the addition polymerization reactor is operated under slurry phase polymerization conditions.

42. The method of claim 40, wherein the addition polymerization reactor is operated under gas phase polymerization conditions.

43. The method of claim 37, wherein the organometal or metalloid compound (c) corresponds to the formula:

$$M^o R^c_x X^a_y,$$

wherein

M$^o$ is a metal or metalloid selected from Groups 1–14 of the Periodic Table of the Elements, R$^c$ independently each occurrence is hydrogen or a group having from 1 to 80 nonhydrogen atoms which is hydrocarbyl, hydrocarbylsilyl, trihydrocarbylsilyl, trihydrocarbylgermyl or hydrocarbylsilylhydrocarbyl;

X$^a$ is a noninterfering group having from 1 to 100 nonhydrogen atoms which is halo-substituted hydrocarbyl, hydrocarbylamino-substituted hydrocarbyl, hydrocarbyloxy-substituted hydrocarbyl, hydrocarbylamino, di(hydrocarbyl)amino, hydrocarbyloxy or halide;

x is a nonzero integer which may range from 1 to an integer equal to the valence of M$^o$;

y is zero or a nonzero integer which may range from 1 to an integer equal to 1 less than the valence of M$^o$; and x+y equals the valence of M$^o$.

44. The method of claim 43, wherein the organometal or metalloid compound is an alumoxane or a mixture of an alumoxane with $M^o R^c_x X_{ay}$.

45. An addition polymerization process wherein one or more addition polymerizable monomers are contacted with a catalyst of claim 10 under addition polymerization conditions.

46. The addition polymerization process of claim 45 which is a solution, slurry phase or gas phase polymerization process.

47. The addition polymerization process of claim 45, wherein the addition polymerization reactor is operated under slurry phase polymerization conditions.

48. The addition polymerization process of claim 45, wherein the addition polymerization reactor is operated under gas phase polymerization conditions.

* * * * *

UNITED STATES PATENT AND TRADEMARK OFFICE
CERTIFICATE OF CORRECTION

PATENT NO. : 6,271,165 B1
DATED : August 7, 2001
INVENTOR(S) : Grant B. Jackson, Pierre H.H. Loix and Theo J.P. Stevens It is certified that error appears in the above-identified patent and that said Letters Patent is hereby corrected as shown below:

<u>Column 50, lines 47-67 and Column 51, lines 1-45,</u>
Please delete Claim 1 in its entirety and replace it with the following:

-- 1. A dispersion of a supported catalyst component comprising (a) an ionic compound comprising (a)(1) a cation and (a)(2) an anion having up to 100 nonhydrogen atoms and the anion containing at least one substituent comprising a moiety having an active hydrogen, and (d) a support material, wherein the supported catalyst component is in solid form dispersed in a diluent in which both (a) and (d) are insoluble or sparingly soluble, and wherein, (i) the support material is a pretreated support material and in the supported catalyst component the anion (a)(2) is not chemically bonded to the support (d), or (ii) the ionic compound has a solubility in toluene at 22ºC of at least 0.1 weight percent, the support material used is a support material containing tethering groups and in the supported catalyst component the anion (a)(2) is chemically bonded to the support (d). --

Signed and Sealed this

First Day of October, 2002

*Attest:*

JAMES E. ROGAN
*Director of the United States Patent and Trademark Office*

*Attesting Officer*